(12) United States Patent
Canovas Vidal et al.

(10) Patent No.: US 10,709,550 B2
(45) Date of Patent: Jul. 14, 2020

(54) PROGRESSIVE POWER INTRAOCULAR LENS, AND METHODS OF USE AND MANUFACTURE

(71) Applicant: AMO Groningen B.V., Groningen (NL)

(72) Inventors: Carmen Canovas Vidal, Groningen (NL); Aixa Alarcon Heredia, Groningen (NL); Patricia Ann Piers, Groningen (NL); Hendrik A. Weeber, Groningen (NL)

(73) Assignee: AMO Groningen B.V., Groningen (NL)

( * ) Notice: Subject to any disclaimer, the term of this patent is extended or adjusted under 35 U.S.C. 154(b) by 8 days.

(21) Appl. No.: 16/042,281

(22) Filed: Jul. 23, 2018

(65) Prior Publication Data

US 2018/0325658 A1 Nov. 15, 2018

Related U.S. Application Data

(62) Division of application No. 15/428,970, filed on Feb. 9, 2017, now Pat. No. 10,028,825.
(Continued)

(51) Int. Cl.
*A61F 2/16* (2006.01)
*G02C 7/04* (2006.01)
(Continued)

(52) U.S. Cl.
CPC ............ *A61F 2/1654* (2013.01); *A61F 2/164* (2015.04); *A61F 2/1618* (2013.01);
(Continued)

(58) Field of Classification Search
CPC ............ G06Q 30/0255; G06Q 30/0272; G06F 16/90324; G06F 16/9535; G06F 16/738; G06F 16/288; G06F 16/285; G06F 16/24
(Continued)

(56) References Cited

U.S. PATENT DOCUMENTS

| 2,077,092 A | 4/1937 | Broder |
| 3,305,294 A | 2/1967 | Alvarez |

(Continued)

FOREIGN PATENT DOCUMENTS

| AU | 735664 B2 | 7/2001 |
| AU | 2010212408 A1 | 9/2010 |

(Continued)

OTHER PUBLICATIONS

"International Search Report and Written Opinion for Application No. PCT/IB2017/000164, dated Jun. 1, 2017, 11 pages."
(Continued)

*Primary Examiner* — Tuyen Tra
(74) *Attorney, Agent, or Firm* — Johnson & Johnson Surgical Vision, Inc.

(57) ABSTRACT

Apparatuses, systems and methods for providing improved intraocular lenses (IOLs), include features for reducing side effects, such as halos, glare and best focus shifts, in multifocal refractive lenses and extended depth of focus lenses. Exemplary ophthalmic lenses can include a continuous, power progressive aspheric surface based on two or more merged optical zones, the aspheric surface being defined by a single aspheric equation. Continuous power progressive intraocular lenses can mitigate optical side effects that typically result from abrupt optical steps. Aspheric power progressive and aspheric extended depth of focus lenses can be combined with diffractive lens profiles to further enhance visual performance while minimizing dysphotopsia effects. The combination can provide an increased depth of focus that is greater than an individual depth of focus of either the refractive profile or the diffractive profile.

35 Claims, 24 Drawing Sheets

Related U.S. Application Data

(60) Provisional application No. 62/293,258, filed on Feb. 9, 2016.

(51) Int. Cl.
*G02C 7/02* (2006.01)
*G02B 27/00* (2006.01)
*G02C 7/06* (2006.01)

(52) U.S. Cl.
CPC ........ *A61F 2/1637* (2013.01); *G02B 27/0075* (2013.01); *G02C 7/027* (2013.01); *G02C 7/028* (2013.01); *G02C 7/04* (2013.01); *G02C 7/044* (2013.01); *G02C 7/066* (2013.01); *G02C 7/068* (2013.01); *G02C 2202/20* (2013.01); *G02C 2202/22* (2013.01)

(58) Field of Classification Search
USPC ................... 351/41, 159.01, 159.73, 159.74
See application file for complete search history.

(56) References Cited

U.S. PATENT DOCUMENTS

| | | |
|---|---|---|
| 3,367,734 A | 2/1968 | Karl et al. |
| 3,735,685 A | 5/1973 | Plummer |
| 4,010,496 A | 3/1977 | Neefe |
| 4,077,071 A | 3/1978 | Freeman |
| 4,093,361 A | 6/1978 | Erickson et al. |
| 4,134,160 A | 1/1979 | Bayers |
| 4,162,122 A | 7/1979 | Cohen |
| 4,174,543 A | 11/1979 | Kelman |
| 4,210,391 A | 7/1980 | Cohen et al. |
| 4,249,272 A | 2/1981 | Poler |
| 4,254,509 A | 3/1981 | Tennant |
| 4,254,510 A | 3/1981 | Tennant |
| 4,316,293 A | 2/1982 | Bayers |
| 4,319,564 A | 3/1982 | Karickhoff |
| 4,338,005 A | 7/1982 | Cohen |
| 4,340,283 A | 7/1982 | Cohen et al. |
| 4,370,760 A | 2/1983 | Kelman |
| 4,377,873 A | 3/1983 | Reichert |
| 4,402,579 A | 9/1983 | Poler |
| 4,403,353 A | 9/1983 | Tennant |
| 4,404,694 A | 9/1983 | Kelman |
| 4,409,691 A | 10/1983 | Levy |
| 4,424,597 A | 1/1984 | Schlegel |
| 4,446,581 A | 5/1984 | Blake |
| 4,480,340 A | 11/1984 | Shepard |
| 4,500,382 A | 2/1985 | Foster |
| 4,504,982 A | 3/1985 | Burk |
| 4,551,864 A | 11/1985 | Akhavi |
| 4,556,998 A | 12/1985 | Siepser |
| 4,560,383 A | 12/1985 | Leiske |
| 4,564,484 A | 1/1986 | Neefe |
| 4,580,882 A | 4/1986 | Nuchman et al. |
| 4,593,981 A | 6/1986 | Scilipoti |
| 4,605,409 A | 8/1986 | Kelman |
| 4,605,411 A | 8/1986 | Fedorov et al. |
| 4,629,460 A | 12/1986 | Dyer |
| 4,629,462 A | 12/1986 | Feaster |
| 4,636,049 A | 1/1987 | Blaker |
| 4,637,697 A | 1/1987 | Freeman |
| 4,642,112 A | 2/1987 | Freeman |
| 4,655,565 A | 4/1987 | Freeman |
| 4,673,406 A | 6/1987 | Schlegel |
| 4,676,791 A | 6/1987 | Lemaster et al. |
| 4,676,792 A | 6/1987 | Praeger |
| 4,681,102 A | 7/1987 | Bartell |
| 4,687,484 A | 8/1987 | Kaplan |
| 4,687,485 A | 8/1987 | Lim et al. |
| RE32,525 E | 10/1987 | Pannu |
| 4,725,277 A | 2/1988 | Bissonette |
| 4,734,095 A | 3/1988 | Siepser |
| 4,769,033 A | 9/1988 | Nordan |
| 4,778,462 A | 10/1988 | Grendahl |
| 4,781,717 A | 11/1988 | Grendahl |
| 4,787,903 A | 11/1988 | Grendahl |
| 4,787,904 A | 11/1988 | Severin et al. |
| 4,795,462 A | 1/1989 | Grendahl |
| 4,798,608 A | 1/1989 | Grendahl |
| 4,798,609 A | 1/1989 | Grendahl |
| 4,828,558 A | 5/1989 | Kelman |
| 4,834,748 A | 5/1989 | McDonald |
| 4,863,539 A | 9/1989 | Lee et al. |
| 4,898,461 A | 2/1990 | Portney |
| 4,906,246 A | 3/1990 | Grendahl |
| 4,932,970 A | 6/1990 | Portney |
| 4,995,714 A | 2/1991 | Cohen |
| 4,995,715 A | 2/1991 | Cohen |
| 4,997,442 A | 3/1991 | Barrett |
| 5,016,977 A | 5/1991 | Baude et al. |
| 5,019,097 A | 5/1991 | Knight et al. |
| 5,047,052 A | 9/1991 | Dubroff |
| 5,050,981 A | 9/1991 | Roffman |
| 5,054,905 A | 10/1991 | Cohen |
| 5,056,908 A | 10/1991 | Cohen |
| 5,066,301 A | 11/1991 | Wiley |
| 5,071,432 A | 12/1991 | Baikoff |
| 5,078,742 A | 1/1992 | Dahan |
| 5,089,023 A | 2/1992 | Swanson |
| 5,096,285 A | 3/1992 | Silberman |
| 5,112,351 A | 5/1992 | Christie et al. |
| 5,114,220 A | 5/1992 | Baude et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,133,749 A | 7/1992 | Nordan |
| 5,144,483 A | 9/1992 | Cohen |
| 5,147,395 A | 9/1992 | Willis |
| 5,147,397 A | 9/1992 | Christ et al. |
| 5,158,572 A | 10/1992 | Nielsen |
| 5,166,711 A | 11/1992 | Portney |
| 5,166,712 A | 11/1992 | Portney |
| 5,181,053 A | 1/1993 | Brown |
| 5,184,405 A | 2/1993 | Cress |
| 5,191,366 A | 3/1993 | Kashiwagi |
| 5,197,981 A | 3/1993 | Southard |
| 5,201,763 A | 4/1993 | Brady et al. |
| 5,203,790 A | 4/1993 | McDonald |
| 5,217,491 A | 6/1993 | Vanderbilt |
| 5,220,359 A | 6/1993 | Roffman |
| 5,225,858 A | 7/1993 | Portney |
| 5,225,997 A | 7/1993 | Lederer et al. |
| 5,229,797 A | 7/1993 | Futhey et al. |
| 5,258,025 A | 11/1993 | Fedorov et al. |
| 5,270,744 A | 12/1993 | Portney |
| 5,278,592 A | 1/1994 | Marie et al. |
| 5,384,606 A | 1/1995 | Koch et al. |
| 5,387,970 A | 2/1995 | Neubert et al. |
| 5,408,281 A | 4/1995 | Zhang |
| 5,433,745 A | 7/1995 | Graham et al. |
| 5,476,513 A | 12/1995 | Brady et al. |
| 5,479,220 A | 12/1995 | Komatsu et al. |
| 5,485,228 A | 1/1996 | Roffman et al. |
| 5,521,656 A | 5/1996 | Portney |
| 5,567,365 A | 10/1996 | Weinschenk, III et al. |
| 5,571,177 A | 11/1996 | Deacon et al. |
| 5,589,024 A | 12/1996 | Blake |
| 5,620,720 A | 4/1997 | Glick et al. |
| 5,628,796 A | 5/1997 | Suzuki |
| 5,652,638 A | 7/1997 | Roffman et al. |
| 5,657,108 A | 8/1997 | Portney |
| 5,684,560 A | 11/1997 | Roffman et al. |
| 5,691,800 A | 11/1997 | Iki et al. |
| 5,699,142 A | 12/1997 | Lee et al. |
| 5,715,031 A | 2/1998 | Roffman et al. |
| 5,716,403 A | 2/1998 | Tran et al. |
| 5,748,282 A | 5/1998 | Freeman |
| 5,754,270 A | 5/1998 | Rehse et al. |
| 5,760,871 A | 6/1998 | Kosoburd et al. |
| 5,766,244 A | 6/1998 | Binder |
| 5,777,719 A | 7/1998 | Williams et al. |

(56) References Cited

U.S. PATENT DOCUMENTS

| | | |
|---|---|---|
| 5,796,462 A | 8/1998 | Roffman et al. |
| 5,798,817 A | 8/1998 | De Carle |
| 5,801,807 A | 9/1998 | Satake et al. |
| 5,864,378 A | 1/1999 | Portney |
| 5,864,379 A | 1/1999 | Dunn |
| 5,877,839 A | 3/1999 | Portney |
| 5,895,422 A | 4/1999 | Hauber |
| 5,919,229 A | 7/1999 | Portney |
| 5,928,282 A | 7/1999 | Nigam |
| 5,968,094 A | 10/1999 | Werblin et al. |
| 6,007,747 A | 12/1999 | Blake et al. |
| 6,015,435 A | 1/2000 | Valunin et al. |
| 6,024,447 A | 2/2000 | Portney |
| 6,030,077 A | 2/2000 | Sawano et al. |
| 6,051,024 A | 4/2000 | Cumming |
| 6,055,111 A | 4/2000 | Nomura et al. |
| 6,082,856 A | 7/2000 | Dunn et al. |
| 6,086,203 A | 7/2000 | Blum et al. |
| 6,126,283 A | 10/2000 | Wen et al. |
| 6,126,286 A | 10/2000 | Portney |
| 6,129,759 A | 10/2000 | Chambers |
| 6,142,625 A | 11/2000 | Sawano et al. |
| 6,176,579 B1 | 1/2001 | Mandell |
| 6,179,870 B1 | 1/2001 | Sourdille et al. |
| 6,186,625 B1 | 2/2001 | Portney |
| 6,210,005 B1 | 4/2001 | Portney |
| 6,221,105 B1 | 4/2001 | Portney |
| 6,224,211 B1 | 5/2001 | Gordon |
| 6,235,055 B1 | 5/2001 | Chu |
| 6,260,966 B1 | 7/2001 | Sawano et al. |
| 6,261,321 B1 | 7/2001 | Kellan |
| 6,286,956 B1 | 9/2001 | Oyama et al. |
| 6,319,282 B1 | 11/2001 | Nishi |
| 6,325,509 B1 * | 12/2001 | Hodur .............. G02C 7/04 351/159.14 |
| 6,338,559 B1 | 1/2002 | Williams et al. |
| 6,390,622 B1 | 5/2002 | Muckenhirn et al. |
| 6,409,339 B1 | 6/2002 | Wanders |
| 6,409,340 B1 | 6/2002 | Portney |
| 6,419,697 B1 | 7/2002 | Kelman |
| 6,428,573 B2 | 8/2002 | Barnett |
| 6,454,408 B1 | 9/2002 | Morris et al. |
| 6,457,826 B1 | 10/2002 | Lett |
| 6,464,355 B1 | 10/2002 | Gil |
| 6,474,814 B1 | 11/2002 | Griffin |
| 6,488,708 B2 | 12/2002 | Sarfarazi |
| 6,491,721 B2 | 12/2002 | Freeman et al. |
| 6,511,178 B1 | 1/2003 | Roffman et al. |
| 6,527,389 B2 | 3/2003 | Portney |
| 6,533,416 B1 | 3/2003 | Fermigier et al. |
| 6,536,899 B1 | 3/2003 | Fiala |
| 6,537,317 B1 | 3/2003 | Steinert et al. |
| 6,540,353 B1 | 4/2003 | Dunn |
| 6,547,822 B1 | 4/2003 | Lang |
| 6,554,859 B1 | 4/2003 | Lang et al. |
| 6,557,992 B1 | 5/2003 | Dwyer et al. |
| 6,596,025 B2 | 7/2003 | Portney |
| 6,598,606 B2 | 7/2003 | Terwee et al. |
| 6,609,793 B2 | 8/2003 | Norrby et al. |
| 6,638,305 B2 | 10/2003 | Laguette |
| 6,663,240 B2 | 12/2003 | Patel |
| 6,705,729 B2 | 3/2004 | Piers et al. |
| 6,709,102 B2 | 3/2004 | Duppstadt |
| 6,764,179 B2 | 7/2004 | Sakai et al. |
| 6,797,003 B1 | 9/2004 | Blake et al. |
| 6,802,605 B2 | 10/2004 | Cox et al. |
| 6,808,262 B2 | 10/2004 | Chapoy et al. |
| 6,814,439 B2 | 11/2004 | Portney |
| 6,830,332 B2 | 12/2004 | Piers et al. |
| 6,846,326 B2 | 1/2005 | Zadno-Azizi et al. |
| 6,851,803 B2 | 2/2005 | Wooley et al. |
| 6,871,953 B1 | 3/2005 | Mandell et al. |
| 6,874,887 B2 | 4/2005 | Tyson |
| 6,883,915 B2 | 4/2005 | Ye et al. |
| 6,899,425 B2 | 5/2005 | Roffman et al. |
| 6,923,539 B2 | 8/2005 | Simpson et al. |
| 6,923,540 B2 | 8/2005 | Ye et al. |
| 6,986,578 B2 | 1/2006 | Jones |
| 7,004,585 B2 | 2/2006 | Lindacher |
| 7,018,409 B2 | 3/2006 | Glick et al. |
| 7,036,931 B2 | 5/2006 | Lindacher et al. |
| 7,040,757 B2 | 5/2006 | Hall et al. |
| 7,048,760 B2 | 5/2006 | Cumming |
| 7,052,133 B2 | 5/2006 | Lindacher et al. |
| 7,061,693 B2 | 6/2006 | Zalevsky |
| 7,073,906 B1 | 7/2006 | Portney |
| 7,080,906 B2 | 7/2006 | Lindacher et al. |
| 7,137,702 B2 | 11/2006 | Piers et al. |
| 7,156,516 B2 | 1/2007 | Morris et al. |
| 7,178,918 B2 | 2/2007 | Griffin |
| 7,188,949 B2 | 3/2007 | Bandhauer et al. |
| 7,204,849 B2 | 4/2007 | Portney |
| 7,241,311 B2 | 7/2007 | Norrby et al. |
| 7,287,852 B2 | 10/2007 | Fiala |
| 7,293,873 B2 | 11/2007 | Dai et al. |
| 7,365,917 B2 | 4/2008 | Zalevsky |
| 7,370,962 B2 | 5/2008 | Roffman et al. |
| 7,377,640 B2 | 5/2008 | Piers et al. |
| 7,381,221 B2 | 6/2008 | Lang et al. |
| 7,441,894 B2 | 10/2008 | Zhang et al. |
| 7,455,404 B2 | 11/2008 | Bandhauer et al. |
| 7,455,407 B2 | 11/2008 | Neal et al. |
| 7,475,986 B2 | 1/2009 | Dai et al. |
| 7,615,073 B2 | 11/2009 | Deacon et al. |
| 7,616,330 B2 | 11/2009 | Neal et al. |
| 7,713,299 B2 | 5/2010 | Brady et al. |
| 7,794,497 B2 | 9/2010 | Brady et al. |
| 7,857,451 B2 | 12/2010 | Thibos et al. |
| 7,871,162 B2 | 1/2011 | Weeber |
| 7,993,398 B2 | 8/2011 | Deacon et al. |
| 8,002,827 B2 | 8/2011 | Deacon et al. |
| 8,018,164 B2 | 9/2011 | Shannon et al. |
| 8,042,942 B2 | 10/2011 | Kaga et al. |
| 8,147,062 B2 | 4/2012 | Kaga et al. |
| 8,162,477 B2 | 4/2012 | Carimalo et al. |
| 8,231,219 B2 | 7/2012 | Weeber |
| 8,240,847 B2 | 8/2012 | Holden et al. |
| 8,241,354 B2 | 8/2012 | Hong et al. |
| 8,382,281 B2 | 2/2013 | Weeber |
| 8,430,508 B2 | 4/2013 | Weeber |
| 8,480,228 B2 | 7/2013 | Weeber |
| 8,529,559 B2 | 9/2013 | Liang |
| 8,573,775 B2 | 11/2013 | Weeber |
| 8,632,187 B1 | 1/2014 | Franques et al. |
| 8,647,383 B2 | 2/2014 | Sanger et al. |
| 8,672,472 B2 | 3/2014 | Holden et al. |
| 8,672,474 B2 | 3/2014 | Lindacher et al. |
| 8,747,466 B2 | 6/2014 | Weeber et al. |
| 8,770,745 B2 | 7/2014 | Lindacher et al. |
| 8,857,982 B2 | 10/2014 | Franques et al. |
| 8,862,447 B2 | 10/2014 | Weeber |
| 8,894,706 B2 | 11/2014 | Portney |
| 8,974,526 B2 | 3/2015 | Bogaert |
| 9,039,172 B2 | 5/2015 | Lindacher et al. |
| 9,265,603 B2 | 2/2016 | Sanger et al. |
| 9,335,563 B2 | 5/2016 | Weeber |
| 9,477,097 B2 | 10/2016 | Holden et al. |
| 2001/0035935 A1 | 11/2001 | Bhalakia et al. |
| 2001/0051825 A1 | 12/2001 | Peterson |
| 2002/0063848 A1 | 5/2002 | Fiala |
| 2002/0118337 A1 | 8/2002 | Perrott et al. |
| 2002/0173846 A1 | 11/2002 | Blake et al. |
| 2002/0196408 A1 | 12/2002 | Bhalakia et al. |
| 2002/0196412 A1 | 12/2002 | Abitbol |
| 2003/0063254 A1 | 4/2003 | Piers et al. |
| 2003/0076478 A1 | 4/2003 | Cox |
| 2003/0171808 A1 | 9/2003 | Phillips |
| 2003/0199976 A1 | 10/2003 | Portney |
| 2004/0054358 A1 | 3/2004 | Cox |
| 2004/0054408 A1 | 3/2004 | Glick et al. |
| 2004/0068317 A1 | 4/2004 | Knight |
| 2004/0085515 A1 | 5/2004 | Roffman et al. |
| 2004/0106992 A1 * | 6/2004 | Lang .............. A61F 2/1618 623/6.28 |

(56) References Cited

U.S. PATENT DOCUMENTS

| | | |
|---|---|---|
| 2004/0111153 A1 | 6/2004 | Woods et al. |
| 2004/0150790 A1 | 8/2004 | Roffman et al. |
| 2004/0156013 A1 | 8/2004 | Lindacher et al. |
| 2004/0156014 A1 | 8/2004 | Piers et al. |
| 2004/0167622 A1 | 8/2004 | Sunalp et al. |
| 2004/0207807 A1 | 10/2004 | Lindacher |
| 2004/0246440 A1 | 12/2004 | Andino et al. |
| 2005/0096226 A1 | 5/2005 | Stock et al. |
| 2005/0125056 A1 | 6/2005 | Deacon et al. |
| 2005/0128432 A1 | 6/2005 | Altmann |
| 2005/0203619 A1 | 9/2005 | Altmann |
| 2005/0251254 A1 | 11/2005 | Brady et al. |
| 2005/0267575 A1 | 12/2005 | Nguyen et al. |
| 2006/0009816 A1 | 1/2006 | Fang et al. |
| 2006/0030938 A1 | 2/2006 | Altmann |
| 2006/0066808 A1 | 3/2006 | Blum et al. |
| 2006/0068453 A1 | 3/2006 | Altieri |
| 2006/0109421 A1 | 5/2006 | Ye et al. |
| 2006/0116763 A1 | 6/2006 | Simpson |
| 2006/0116764 A1 | 6/2006 | Simpson |
| 2006/0116765 A1 | 6/2006 | Blake et al. |
| 2006/0238702 A1 | 10/2006 | Glick et al. |
| 2006/0244904 A1 | 11/2006 | Hong et al. |
| 2006/0244916 A1 | 11/2006 | Guillon |
| 2006/0279700 A1 | 12/2006 | Liang |
| 2007/0052920 A1 | 3/2007 | Stewart et al. |
| 2007/0129803 A1 | 6/2007 | Cumming et al. |
| 2007/0171362 A1 | 7/2007 | Simpson et al. |
| 2007/0182924 A1 | 8/2007 | Hong et al. |
| 2007/0258143 A1 | 11/2007 | Portney |
| 2007/0268453 A1 | 11/2007 | Hong et al. |
| 2008/0018910 A1 | 1/2008 | Neal et al. |
| 2008/0030677 A1 | 2/2008 | Simpson |
| 2008/0161914 A1 | 7/2008 | Brady et al. |
| 2008/0231809 A1 | 9/2008 | Haigis |
| 2008/0273169 A1 | 11/2008 | Blum et al. |
| 2008/0291393 A1 | 11/2008 | Menezes |
| 2009/0012609 A1 | 1/2009 | Geraghty et al. |
| 2009/0036980 A1 | 2/2009 | Norrby et al. |
| 2009/0051870 A1 | 2/2009 | Lindacher et al. |
| 2009/0051876 A1 | 2/2009 | Seiler et al. |
| 2009/0062911 A1 | 3/2009 | Bogaert |
| 2009/0088840 A1 | 4/2009 | Simpson et al. |
| 2009/0164008 A1 | 6/2009 | Hong et al. |
| 2009/0210054 A1 | 8/2009 | Weeber et al. |
| 2009/0234448 A1 | 9/2009 | Weeber et al. |
| 2009/0279048 A1 | 11/2009 | Hong et al. |
| 2009/0303433 A1 | 12/2009 | Shimojo |
| 2009/0323020 A1 | 12/2009 | Zhao et al. |
| 2010/0016965 A1 | 1/2010 | Hong et al. |
| 2010/0036489 A1 | 2/2010 | Lindacher et al. |
| 2010/0066973 A1 | 3/2010 | Portney |
| 2010/0082017 A1 | 4/2010 | Zickler et al. |
| 2010/0097569 A1 | 4/2010 | Weeber et al. |
| 2010/0100178 A1 | 4/2010 | Weeber et al. |
| 2010/0161048 A1 | 6/2010 | Schaper, Jr. |
| 2010/0161051 A1 | 6/2010 | Hong |
| 2010/0274234 A1 | 10/2010 | Liang |
| 2010/0315589 A1 | 12/2010 | Portney |
| 2012/0140166 A1 | 6/2012 | Zhao |
| 2012/0143326 A1 | 6/2012 | Canovas Vidal et al. |
| 2012/0320334 A1 | 12/2012 | Ho et al. |
| 2014/0135919 A1 | 5/2014 | Gontijo et al. |
| 2014/0168602 A1 | 6/2014 | Weeber et al. |
| 2015/0182329 A1 | 7/2015 | Bogaert |
| 2015/0297343 A1 | 10/2015 | Hehn |
| 2015/0342727 A1 | 12/2015 | Fernández et al. |
| 2016/0062144 A1 | 3/2016 | Brennan et al. |
| 2016/0062145 A1 | 3/2016 | Brennan et al. |
| 2016/0299355 A1 | 10/2016 | Biemold et al. |
| 2017/0216020 A1 | 8/2017 | Weeber et al. |

FOREIGN PATENT DOCUMENTS

| | | |
|---|---|---|
| AU | 2012362545 B2 | 7/2015 |
| CA | 2722274 A1 | 10/2009 |
| CA | 2787997 C | 2/2015 |
| CA | 2901889 A1 | 2/2016 |
| CN | 1035363 A | 9/1989 |
| CN | 1039487 A | 2/1990 |
| CN | 1406120 A | 3/2003 |
| CN | 1833192 A | 9/2006 |
| DE | 8107675 U1 | 7/1981 |
| DE | 3439551 A1 | 4/1986 |
| EP | 226400 A2 | 6/1987 |
| EP | 227357 A2 | 7/1987 |
| EP | 0343067 A1 | 11/1989 |
| EP | 0457553 A2 | 11/1991 |
| EP | S81198 A1 | 11/1995 |
| EP | 742466 A2 | 11/1996 |
| EP | 900403 A1 | 3/1999 |
| EP | 0926531 A1 | 6/1999 |
| EP | 949529 A2 | 10/1999 |
| EP | 957331 A2 | 11/1999 |
| EP | 1424049 A1 | 6/2004 |
| EP | 1310267 B1 | 1/2008 |
| EP | 2033596 A1 | 3/2009 |
| EP | 1424049 B1 | 6/2009 |
| EP | 2182891 B1 | 4/2014 |
| FR | 2745711 A1 | 9/1997 |
| JP | H0255314 A | 2/1990 |
| JP | 4126144 A2 | 4/1992 |
| JP | 11503250 T | 3/1999 |
| JP | 2000511439 T2 | 9/2000 |
| JP | 2004537332 A | 12/2004 |
| WO | 8603961 A1 | 7/1986 |
| WO | 8700299 A1 | 1/1987 |
| WO | 8809950 A1 | 12/1988 |
| WO | 9222000 A1 | 12/1992 |
| WO | 9222264 A1 | 12/1992 |
| WO | 9303409 A1 | 2/1993 |
| WO | 9507487 A1 | 3/1995 |
| WO | 9856315 A1 | 12/1998 |
| WO | 0008516 A | 2/2000 |
| WO | 0019906 A1 | 4/2000 |
| WO | 0111418 A1 | 2/2001 |
| WO | 0135868 A1 | 5/2001 |
| WO | 0154569 A1 | 8/2001 |
| WO | 0163344 A1 | 8/2001 |
| WO | 0182839 A1 | 11/2001 |
| WO | 0189424 A1 | 11/2001 |
| WO | 0221194 A2 | 3/2002 |
| WO | 02074210 A2 | 9/2002 |
| WO | 02084381 A2 | 10/2002 |
| WO | 03009053 A1 | 1/2003 |
| WO | 02084381 A3 | 10/2003 |
| WO | 2004034129 A1 | 4/2004 |
| WO | 2004068214 A1 | 8/2004 |
| WO | 04089252 A2 | 10/2004 |
| WO | 2004090611 A2 | 10/2004 |
| WO | 2004096014 A2 | 11/2004 |
| WO | 05019906 A1 | 3/2005 |
| WO | 06025726 A1 | 3/2006 |
| WO | 2006032263 A2 | 3/2006 |
| WO | 2006047698 A1 | 5/2006 |
| WO | 06060477 A2 | 6/2006 |
| WO | 2006060480 A2 | 6/2006 |
| WO | 2007067872 A2 | 6/2007 |
| WO | 2007092948 A1 | 8/2007 |
| WO | 2007133384 A2 | 11/2007 |
| WO | 2008045847 A2 | 4/2008 |
| WO | 2008083283 A2 | 7/2008 |
| WO | 2009017403 A1 | 2/2009 |
| WO | 2009020963 A1 | 2/2009 |
| WO | 2009029515 A1 | 3/2009 |
| WO | 2009058755 A1 | 5/2009 |
| WO | 2009076670 A1 | 6/2009 |
| WO | 2009137491 A1 | 11/2009 |
| WO | 2010009254 A1 | 1/2010 |
| WO | 2010009257 A1 | 1/2010 |
| WO | 2010054255 A1 | 5/2010 |

(56) References Cited

FOREIGN PATENT DOCUMENTS

| WO | 2013018379 A1 | 2/2013 |
|---|---|---|
| WO | 2014033543 A2 | 3/2014 |
| WO | 2014033543 A3 | 6/2014 |

OTHER PUBLICATIONS

International Search Report and Written Opinion for Application No. PCT/IB2017/000170, dated May 30, 2017, 14 pages.
International Search Report and Written Opinion for Application No. PCT/IB2017/000173, dated May 30, 2017, 11 pages.
Alfonso J.F., et al., "Prospective Study of the Acri.LISA Bifocal Intraocular Lens," Journal of Cataract Refractive Surgery, Nov. 2007, vol. 33 (11), pp. 1930-1935.
Alio J.L., et al., "Phakic Anterior Chamber Lenses for the Correction of Myopia: A 7-Year Cumulative Analysis of complications in 263 Cases," Ophthalmology, Mar. 1999, vol. 106 (3), pp. 458-466.
Apple D.J., et al., "Anterior Chamber Lenses Part 1: Complications and Pathology and a Review of Designs," Journal of Cataract Refractive Surgery, Mar. 1987, vol. 13 (2), pp. 157-174.
Apple D.J., et al., Eds., "Intraocular Lenses: Evolution, Designs, Complications and Pathology," in: New Concepts in Intraocular Lens Implantation, Williams & Wilkins publisher, Jan. 1989, vol. 22 (36), pp. 205-221.
Apple D.J., et al., Eds., "Intraocular Lenses: Evolution, Designs, Complications and Pathology," in: New Concepts in Intraocular Lens Implantation, Williams & Wilkins publisher, Jan. 1989, vol. 36 (1), pp. 21-36.
Atchinson D.A., "Optical Design of Intraocular Lenses. I. On-Axis Performance," American Academy of Optometry, 1989, vol. 66 (8), pp. 492-506.
Baikoff G., et al., "Angle-fixated Anterior Chamber Phakic Intraocular Lens for Myopia 7 to -19 Diopters," Journal of Refractive Surgery, May-Jun. 1998, vol. 14 (3), pp. 282-292.
Canovas C., et al., "Hybrid Adaptive-Optics Visual Simulator," Optical Letters, Jan. 15, 2010, vol. 35 (2), pp. 196-198.
Cheng X., et al., "Predicting Subjective Judgment of Best Focus with Objective Image Quality Metrics," Journal of Vision, Apr. 2004, vol. 4 (4), pp. 310-321.
CILCO Advertisement Brochure, Oct. 1982, 3 pages.
Cohen A.L., "Practical Design of a Bifocal Hologram Contact Lens or Intraocular Lens," Applied Optics, Jul. 1, 1992, vol. 31 (19), pp. 3750-3754.
De Almeida M.S., et al., "Different Schematic Eyes and their Accuracy to the in Vivo Eye: A Quantitative Comparison Study," Brazilian Journal of Physics, Jun. 2007, vol. 37 (2A), 10 pages.
Diffractive Lenses for Extended Depth of Focus and Presbyopic Correction, Presentation from Wavefront Congress held on Feb. 15, 2008, Rochester, New York.
Doskolovich L.L., et al., "Special Diffractive Lenses," Lens and Optical Systems Design, Apr. 1992, vol. 1780, pp. 393-402.
Kim J.H., et al., "The Analysis of Predicted Capsular Bag Diameter using Modified Model of Capsule Measuring Ring in Asians," Clinical and Experimental Ophthalmology, Apr. 2008, vol. 36 (3), pp. 238-244.
Liou H.L., et al., "Anatomically Accurate, Finite Model Eye for Optical Modeling," Journal of Optical Society of America, Aug. 1997, vol. 14 (8), pp. 1684-1695.
Liou H.L., et al., "The Prediction of Spherical Aberration with Schematic Eyes," Ophthalmic and Physiological Optics, Jan. 1996, vol. 16 (4), pp. 348-354.
Marinho A., "Results are Encouraging for Phakic IOLs, but More Work is needed," Refractive Surgery, Feb. 2000, p. 12, 15.
Marsack J.D., et al., "Metrics of Optical Quality Derived from Wave Aberrations Predict Visual Performance," Journal of Vision, Apr. 2004, vol. 4 (4), pp. 322-328.
Menapace R., "The Capsular Tension Rings," Journal of Cataract & Refractive Surgery, Dec. 10, 2008, Chap. 3, pp. 27-44.
Monsoriu J.A., et al., "Devil's Lenses," Optics Express, Oct. 17, 2007, vol. 15 (21), pp. 13858-13864.
Navarro R., et al., "Accommodation-Dependent Model of the Human Eye with Aspherics," Journal of the Optical Society of America, Aug. 1985, vol. 2 (8), pp. 1273-1281.
Nio Y.K., et al., "Effect of Intraocular Lens Implantation on Visual Acuity, Contrast Sensitivity, and Depth of Focus," Journal of Cataract and Refractive Surgery, Nov. 2003, vol. 29 (11), pp. 2073-2081.
Norrby S., et al., "Model Eyes for Evaluation of Intraocular Lenses," Applied Optics, Sep. 7, 2007, vol. 46 (26), pp. 6595-6605.
Olsen T., "Simple Method to Calculate the Surgically Induced Refractive Change," Journal of Cataract & Refractive Surgery, Mar. 1993, vol. 19 (2), pp. 319-320.
Packer M., et al., "Prospective Randomized Trial of an Anterior Surface Modified Prolate Intraocular Lens," Journal of Refractive Surgery. 2002, vol. 18 (6), pp. 692-696.
Piers P.A., et al., "Eye Models for the Prediction of Contrast Vision in Patients with New Intraocular Lens Designs," Optics Letters, Apr. 1, 2004, vol. 29 (7), pp. 733-735.
Piers P.A., et al., "Theoretical Comparison of Aberration-Correcting Customized and Aspheric Intraocular Lenses," Journal of Refractive Surgery, Apr. 2007, vol. 23 (4), pp. 374-384.
Praeger D.L., "Praeger Technique for the Insertion of the Copeland Radial IOL Posterior Chamber Placement," Copeland Lens, 1982, 7 pages.
Siedlecki D., et al., "Radial Gradient index Intraocular Lens: a Theoretical Model," Journal of Modem Optics, Feb. 20-Mar. 10, 2008, vol. 55 (4-5), pp. 639-647.
Strenn K., et al., "Capsular bag Shrinkage after Implantation of an Open-Loop Silicone Lens and a Poly(methyl methacrylate) Capsule Tension Ring," Journal of Cataract and Refractive Surgery, Dec. 1997, vol. 23 (10), pp. 1543-1547.
Tehrani M., et al., "Capsule Measuring Ring to Predict Capsular Bag Diameter and Follow its Course after Foldable Intraocular Lens Implantation," Journal of Cataract Refractive Surgery, Nov. 2003, vol. 29 (11), pp. 2127-2134.
Terwee T., et al., "Visualization of the Retinal Image in an Eye Model With Spherical and Aspheric, Diffractive, and Refractive Multifocal Intraocular Lenses," Journal of Refractive Surgery, Mar. 2008, vol. 24 (3), pp. 223-232.
Van Den Berg T.J., "Analysis of Intraocular Straylight, Especially in Relation to Age," Optometry and Vision Science, Feb. 1995, vol. 72 (2), pp. 52-59.
Van Meeteren A., "Calculations on the Optical Modulation Transfer Function of the Human Eye for White Light," Optica Acta, May 1974, vol. 21 (5), pp. 395-412.
Vass C., et al., "Prediction of Pseudophakic Capsular bag Diameter based on Biometric Variables," Journal of Cataract and Refractive Surgery, Oct. 1999, vol. 25 (10), pp. 1376-1381.
Venter, J.A., et al., "Visual Outcomes and Patient Satisfaction with a Rotational Asymmetric Refractive Intraocular Lens for Emmetropic Presbyopia," Cataract & Refractive Surgery, Mar. 2015, vol. 41 (3), pp. 585-593.
Villegas E.A., et al., "Correlation between Optical and Psychophy, Sical Parameters as a Function of Defocus," Optometry and Vision Science, Jan. 1, 2002, vol. 79 (1), pp. 60-67.
Wolffsohn J.S., et al., "Visual Function in Patient's Implanted with a Non-Concentric Multifocal Intraocular Lens," 2010.
Zemax, Optical Design Program User's Guide, Nov. 1, 2004, Part 1 of 2 and Chapter 1-11, Retrieved from the Internet: URL: www.itsabook.com.

* cited by examiner

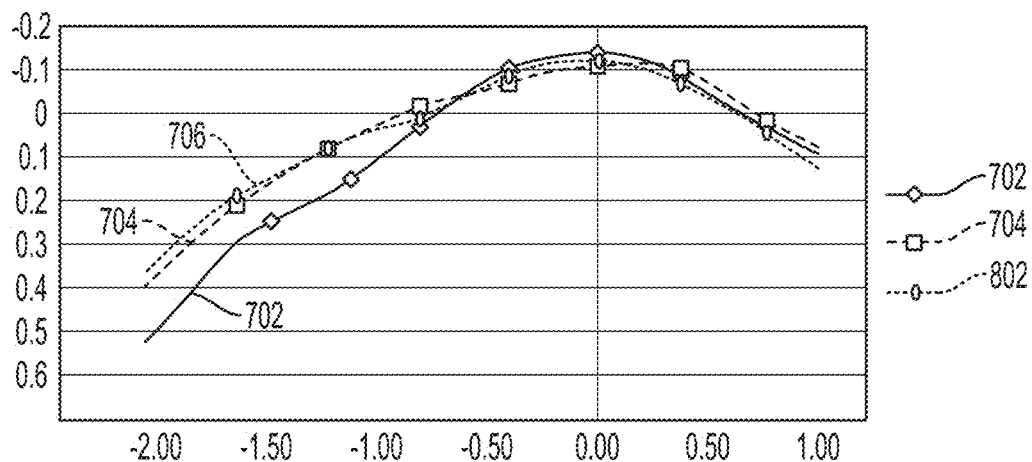
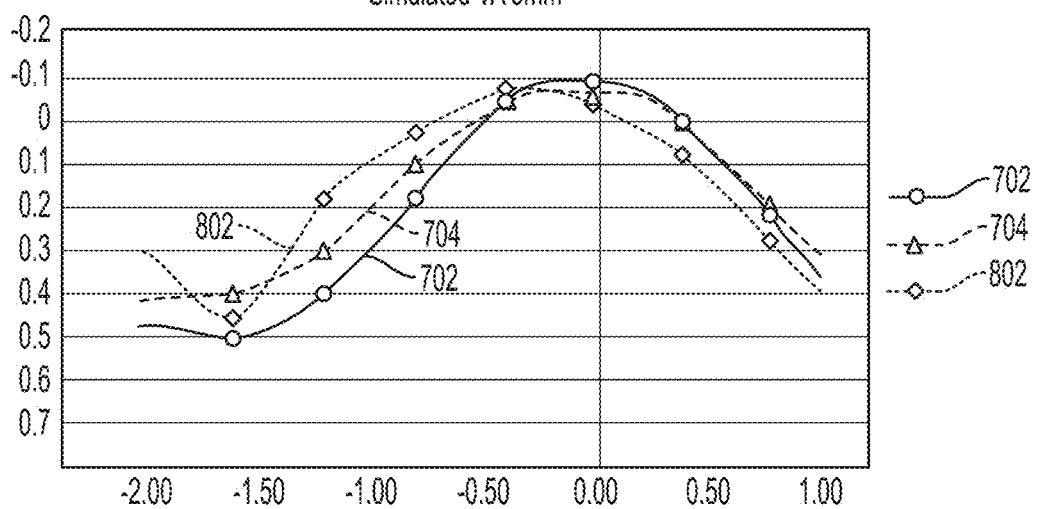

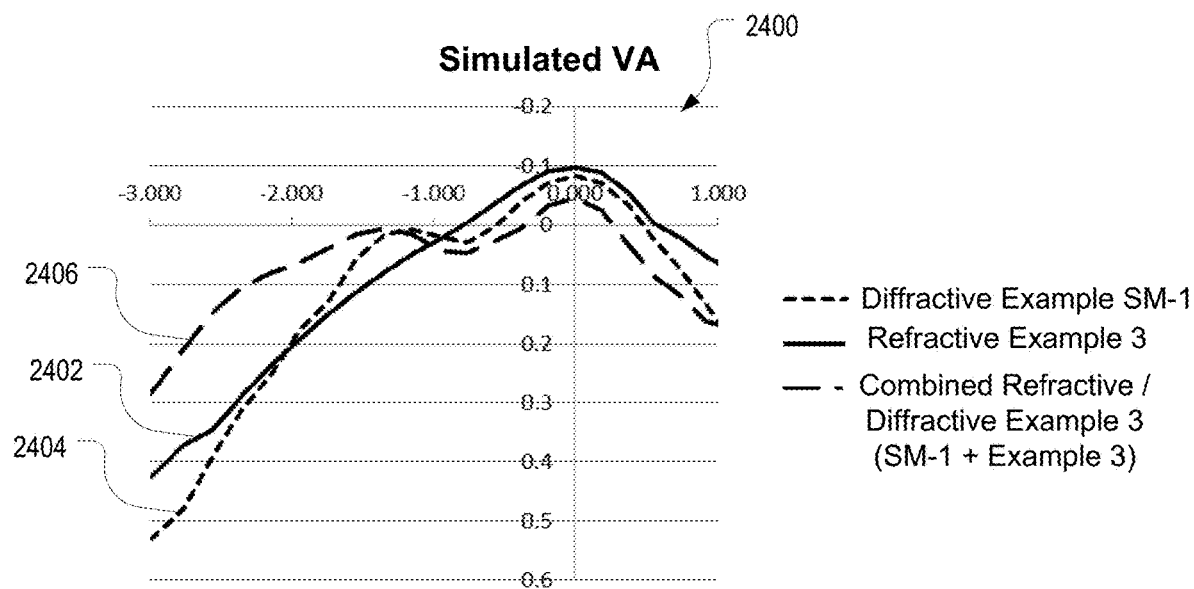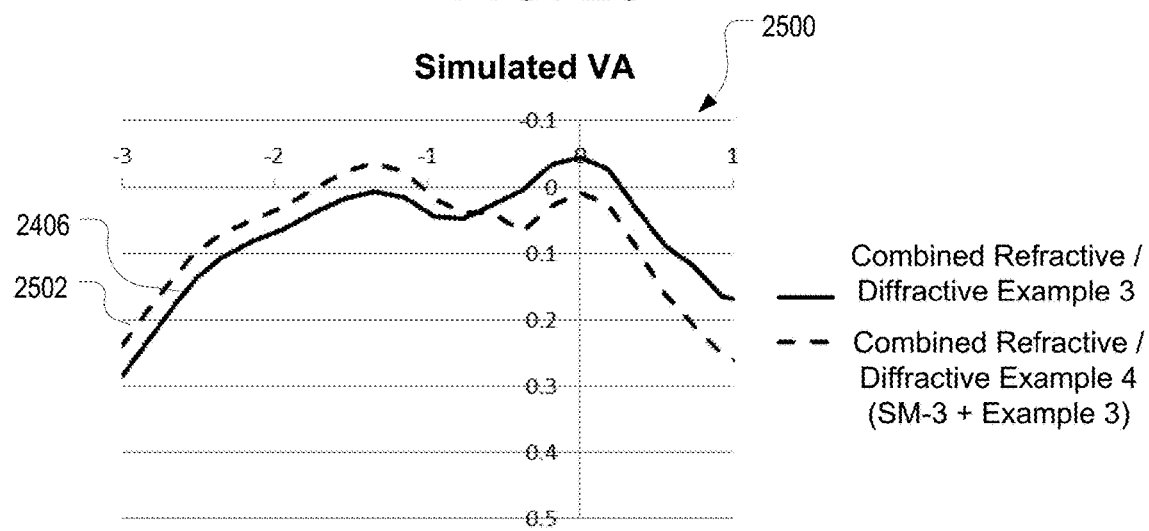

PROGRESSIVE POWER INTRAOCULAR LENS, AND METHODS OF USE AND MANUFACTURE

CROSS-REFERENCES TO RELATED APPLICATIONS

This application claims priority to and is a divisional application of U.S. patent application Ser. No. 15/428,970, filed Feb. 9, 2017, which claims the benefit of U.S. Provisional Patent Application No. 62/293,258 filed Feb. 9, 2016 entitled "Progressive Power Intraocular Lens, and Methods of Use and Manufacture." The content of the above listed application is incorporated herein by reference.

BACKGROUND OF THE INVENTION

Embodiments of the present invention relate generally continuous power progressive lens surfaces, and particular embodiments provide methods, devices, and systems for mitigating or treating vision conditions such as presbyopia, often by determining a desired power ranges for the profile and selecting an aspheric surface that results in a continuous power progressive lens shape according to the desired power profile and to various parameters of the patient's eye.

In multifocal intraocular lenses (IOLs), multiple optical zones provide for different optical powers at the different zones. The multiple optical zones can improve the vision of a patient at different viewing distances, such as near distance, intermediate distance and far distance. A neuroadaptation phenomenon allows the human brain to choose which focused image to rely on out of multiple focal distances provided. Therefore, an implanted intraocular lens with multiple zones can allow a patient to see with improved acuity at multiple viewing distances. However, multifocal intraocular lenses can also reduce the contrast on the image, and can increase night vision disturbances such as glare and halo. Moreover, multifocal IOLs can also cause best focus shift under different light conditions.

Although current and proposed multifocal intraocular lenses and related methods provide real benefits to patients in need thereof, still further advances would be desirable. Embodiments of the present invention provide solutions to at least some of these outstanding needs.

BRIEF SUMMARY OF THE INVENTION

Embodiments herein described include IOLs with a continuous refractive aspheric surface that results in a radial power progression. Specific embodiments include IOLs with an aspheric surface defined by a single aspheric equation that includes certain high order terms. Such IOL's can approximate some features of a multifocal lens providing a range of powers, but without some of the drawbacks associated with multifocal lenses. In one example, an aspheric IOL can approximate a first optical zone across a first region of the IOL and approximate a second optical zone across a second region of the IOL. The continuous aspheric surface of the IOL lacks the discontinuity associated with a multizonal surface. Advantageously, IOL embodiments disclosed herein provide improved optical performance in low-light or night viewing conditions by avoiding or reducing side effects, including visual artifacts such as glare and halo, as well as best focus shifts and contrast sensitivity loss. Visual artifacts are often perceived by patients treated with currently available multifocal IOLs, and are typically produced by point sources of light, such as automobile headlights and traffic or street lights.

IOL embodiments disclosed herein avoid the use of certain physical transitions between different optical zones that can otherwise create or exacerbate visual artifacts for the patient. Optical power can be determined, e.g., by the optical shape of a lens. In general, optical power is related to the second derivative or curvature of an optical shape. For example, power can be defined in terms of an instantaneous radius of curvature or an axial radius of curvature. In a refractive multifocal IOL, different regions of a lens surface have different curvatures. For example, in certain annular designs, concentric annular optical zones may each be configured to maintain a different predefined focal length to enable multifocal vision. However, the annular zones would tend to meet at abrupt changes in curvature. An abrupt optical power step between adjacent zones can cause visual artifacts including glare, halos, and decreased contrast sensitivity. Although the effects of zone boundaries can be reduced by inserting matching transition zones, such transitions zones can also introduce dysphotopsia effects. Visual artifacts can be compounded when the number of different zones (and accordingly the number of abrupt optical power steps) is increased.

IOL embodiments according to the present invention avoid the abrupt changes in curvature described above. For example, IOLs having a surface defined by a continuous aspheric function, which have a continuous first derivative and a continuous second derivative, can further reduce or eliminate visual artifacts and other dysphotopsia effects. In some cases, progressive power IOLs having a continuous aspheric surface can achieve visual performance that reduces dysphotopsia effects to levels similar to an aspheric monofocal lens. Furthermore, IOL embodiments according to the present invention can provide desirable visual performance attributes at intermediate viewing distances, whereas some currently available IOLs are limited to only providing for near and far vision.

IOL embodiments described herein can be configured to approximate multizonal designs by having a continuous aspheric curvature fitted to a multizonal surface. In some cases, an IOL can approximate multiple annular zones in a radial power progressive design fitted to an aspheric surface. The continuous power progressive IOLs achieve good visual performance in both the far and intermediate distances, while reducing visual artifacts and optical aberrations. In some cases, such IOLs can be configured to induce or to alleviate specific optical aberrations. For example, a multizonal surface can be fitted to the continuous aspheric surface, thus eliminating abrupt optical steps that would otherwise exist between zones, providing improved focal depth at specified distances for different pupil sizes, or mitigating visual artifacts such as halos, glare, and reduced contrast sensitivity. In addition, fitting procedures can generate IOLs that have improved cosmetic appearance over IOLs with discrete optical zones, thus generating IOLs that may be visually indistinguishable from monofocal IOLs.

For IOL embodiments that approximate multizonal configurations, the number of zones and power, diameter, and spherical aberration of each zone can be modified to provide different performance attributes for distance, intermediate, and/or near vision at different pupil sizes, prior to generating a continuous aspheric lens surface. For example, lens attributes may be adjusted to provide increased depth of focus, i.e. providing acceptable image sharpness for a patient across a greater range of distances, without significantly increasing visual artifacts or refractive errors. Furthermore, lens attributes may be adjusted to increase depth of focus while taking into account and accommodating specific pupil sizes. Also, various designs herein described provide continuous vision within a range of defocus values, and are therefore more tolerant than conventional IOLs to residual refractive errors within the range. Moreover, IOL embodiments disclosed herein may also compensate for best focus shift for different light conditions.

According to some aspects, embodiments of the present invention can include systems and methods for generating a continuous aspheric surface for use in continuous aspheric implantable lenses. In some cases, methods for generating a continuous aspheric surface can include defining a first optical zone configured to place a first focal distance of the intraocular lens a first distance behind the intraocular lens, and defining a second optical zone configured to place a second focal distance of the intraocular lens, a second distance behind the intraocular lens. The first and second optical zones can be determined based on criteria such as, but not limited to, choosing optical performance for specific distances or depths of focus, for accommodating a specific pupil size, or other visual needs.

In embodiments, systems and methods for generating the continuous aspheric surface can include generating the continuous aspheric surface from an elevation profile of the optical zones. The first optical zone can have an elevation profile that extends from a center of the first optical zone to an outer periphery of the first optical zone. The second optical zone can have an elevation profile that extends from an inner periphery of the second optical zone to an outer periphery of the second optical zone. An elevation step disposed between the profiles can be eliminated by merging the optical zones at the zone boundary. An optical power step disposed between the power profile of the first optical zone and the power profile of the second optical zone can be eliminated by generating the aspheric surface for the intraocular lens based on the fitting of the merged first optical zone and second optical zone.

In embodiments, the aspheric surface may be defined by a single aspheric equation, such that the continuous aspheric surface for the intraocular lens approximates aspects of the first optical zone across a first region of the intraocular lens and approximates aspects of the second optical zone across a second region of the intraocular lens. Such aspects can include the optical powers across portions of the optical zones, asphericity and the elevation across portions of the optical zones. The single aspheric equation can define the continuous aspheric surface such that the optical power of an intraocular lens produced with the surface varies as a continuous function of the radial distance from the center of the intraocular lens, such that there is no optical power step along the intraocular lens power profile.

According to some aspects, embodiments of the present invention can include systems for making a continuous aspheric implantable lens. Such systems can include an input that accepts an ophthalmic lens prescription for a patient eye. Suitable ophthalmic lens prescriptions may provide a first optical power or range of powers for defining a first region of an implantable lens and a second optical power or range of powers for defining a second region of the implantable lens. In some cases, prescriptions can provide multiple optical powers or ranges of optical powers for defining more than two regions of an implantable lens. Such systems may also include one or more modules for generating an aspheric curvature based on the ophthalmic lens prescription. In some cases, the aspheric curvature can be configured to fit the merged first region and the second region. Such systems may further include a manufacturing assembly, such as a computer-controlled fabrication module, that fabricates the intraocular lens based on the aspheric curvature.

According to some embodiments of the present invention, ophthalmic lenses having a continuous aspheric refractive power profile can be combined with diffractive profiles to achieve an extended depth of focus. For example, an ophthalmic lens can have a first surface and a second surface disposed about an optical axis, the lens being characterized by an extended depth of focus. A refractive profile, which can be a continuous aspheric refractive power-progressive profile, is imposed on one of the first surface or the second surface; and a diffractive profile can be imposed on one of the first surface or the second surface. In some cases, the diffractive profile and refractive profile can be on the same surface; or in some cases they can be on opposite surfaces. For example, in some embodiments, diffractive and refractive profiles can be on a posterior surface; or in other embodiments, the diffractive profile can be on a posterior surface and the refractive profile on the anterior surface. The diffractive profile includes at least one set of diffractive zones that partially corrects for ocular chromatic aberration. The combination of the refractive profile and diffractive profile provides an increased depth of focus that is greater than an individual depth of focus of either the refractive profile or the diffractive profile.

For a fuller understanding of the nature and advantages of the present invention, reference should be made to the ensuing detailed description taken in conjunction with the accompanying drawings.

BRIEF DESCRIPTION OF THE DRAWINGS

FIGS. 8A-8B show the simulated visual acuity of an additional example lens for pupil sizes of 3 mm and 5 mm, respectively, similar to FIGS. 7A-7B;

FIG. 24 shows simulated VA of an example combined power progressive/diffractive EDF lens with comparative plots illustrating simulated VA of a power progressive lens and of a diffractive EDF lens, according to some embodiments;

FIG. 25 shows simulated VA of example combined power progressive/diffractive EDF lenses, according to some embodiments;

DETAILED DESCRIPTION OF THE INVENTION

Figure 1:
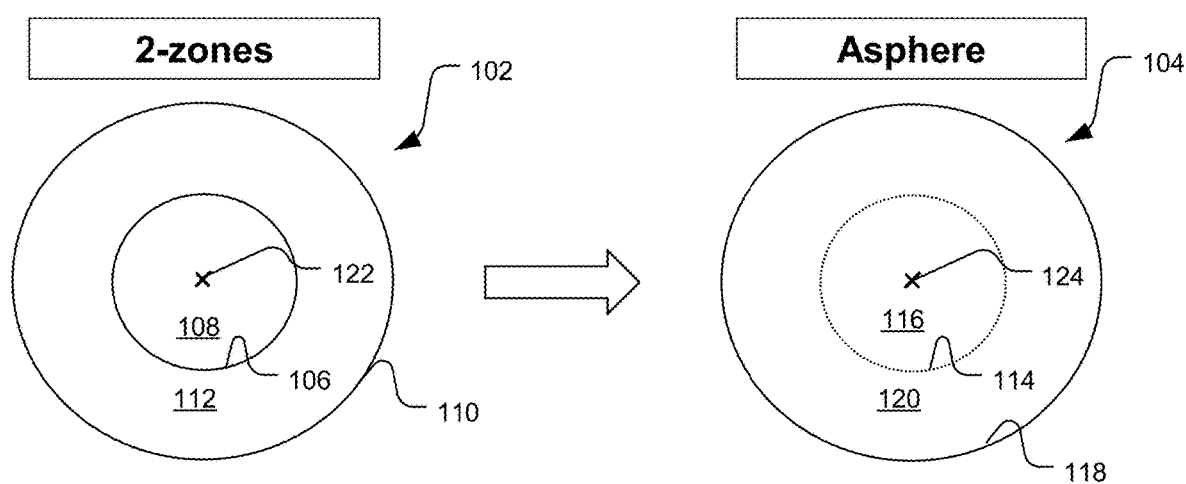
FIG. 1 illustrates a multizonal surface and an analogous progressive power lens approximating the multizonal surface in a front view, in accordance with embodiments.

Embodiments herein disclosed relate to lenses having refractive power-progressive profiles, e.g., lenses having a refractive aspheric profile that provides a continuous power progression to extend depth of focus (EDF). Some embodiments herein disclosed relate to lenses having refractive power-progressive profiles in conjunction with diffractive profiles, which provide improved depth of focus to a patient. According to some embodiments, a diffractive lens can partially correct for ocular chromatic aberration.

Embodiments of lenses herein disclosed can be configured for placement in the eye of a patient and aligned with the cornea to augment and/or partially replace the function of the crystalline lens. In some embodiments, corrective optics may be provided by phakic IOLs, which can be used to treat patients while leaving the natural lens in place. Phakic IOLs may be angle supported, iris supported, or sulcus supported. IOLs can be further secured with support members that attach the IOL to the eye, e.g., with physical extensions from the IOL into adjacent corneal or iris tissue. Phakic IOLs can also be placed over the natural crystalline lens or piggy-backed over another IOL. Exemplary ophthalmic lenses include contact lenses, phakic lenses, pseudophakic lenses, corneal inlays, and the like. It is also envisioned that the lens shapes disclosed herein may be applied to inlays, onlays, accommodating IOLs, spectacles, and even laser vision correction.

In various embodiments, an intraocular lens can include a first region having a nonzero relative power respect to the base power of the lens and a second region defining a base power that extends to the periphery of the lens. The first region can be radially symmetric about an optical axis of the lens and extend part of a distance from the axis to the periphery. The second region can be an aspheric surface which extends from the outer diameter of the first region to the lens periphery. The second region can have a relative power of approximately zero throughout substantially all of the zone while exhibiting aspheric profile configured to match the elevations of the first region at the first region outer diameter, such that the first and second regions merge smoothly at the boundary between the zones. In embodiments, the first and second regions can be described by a unique surface function, such that there are no discontinuities or abrupt breaks in an add profile across the lens. Regions can be defined as portions of the lens described by the radius of the zones that are fitted to the aspheric equation. Therefore, region boundaries need not equate to physical boundaries because the lens has a continuous curvature. However, the surface function can include high-order terms in order to provide optical properties that functionally approximate an intraocular lens having discrete optical zones.

In various embodiments, an intraocular lens can include regions in addition to the first and second regions that have nonzero relative powers respect to the base power of the lens. In one example, a first region can include a range of relative powers for providing near vision in a patient with presbyopia, and a second region can include a range of relative powers for correcting intermediate vision in the same patient. The first and second regions can be positioned in a radially symmetric manner about an optical axis, with the third region being positioned around the first and second regions. The third region, which can be defined by the same surface function which defines the first and second regions, can define the base power of the lens (i.e. have an relative power of approximately zero) throughout substantially all of the zone while exhibiting aspheric curvature configured to match the elevations of the second region, such that the second and third regions merge smoothly. Elevations resulting from merging the first, second and third zones are determined, and then fitted to a unique aspheric surface. The continuous aspheric surface approximates some attributes of the original zones, but results in a continuous surface that prevents or mitigates dysphotopsia and optical effects that would ordinarily result from connecting discrete optical zones. In some other embodiments, multiple intermediate regions having different optical power ranges can be provided between the center of an intraocular lens and its periphery.

Exemplary Intraocular Lens Shapes Approximating 2-Zone Surface:

Turning now to the drawings, FIG. 1 illustrates a multizonal surface 102 and an analogous, continuous power progressive intraocular lens surface 104 based on the multizonal surface in a front view, in accordance with embodiments. The multizonal surface 102 includes two concentric lens surfaces defining a first zone 108 that is concentric and radially symmetric about an optical axis 122, and a second zone 112 that is concentric with the first zone and also radially symmetric about the optical axis. The original, multizonal surface can be described according to the following dimensions in Table 1:

TABLE 1

Lens parameters of an exemplary multizonal lens.

| Zone 1 (spherical) | | Zone 2 (aspheric) | |
| --- | --- | --- | --- |
| Relative power | Extension (diameter) | Relative power | Extension (diameter) |
| 2.3 D | 1 mm | 0 D | 5 mm |

Each zone can be defined according to the aspheric equation for lens sag, as follows:

High-order aspheric equation for an intraocular lens.

$$Z = \frac{cr^2}{1 + \sqrt{1 - (k+1)c^2 r^2}} + a_2 r^2 + a_4 r^4 + a_6 r^6 + a_8 r^8 + a_{10} r^{10} + a_{12} r^{12} + z_0 \quad \text{Equation 1}$$

In the equation above 'r' is the radial distance in mm, 'c' is the curvature in mm$^{-1}$, 'k' is the conic constant, and $a_2$, $a_4$, $a_6$, $a_8$, $a_{10}$, $a_{12}$ are aspheric coefficients; and $z_0$ is an elevation parameter referring to an elevation of the aspheric surface. The elevation parameters of two or more surfaces may be adjusted without changing the shapes of the surfaces to smoothly merge both zones, such that an elevation step that may be present between the two zones is eliminated. This parameter directly depends on the geometry of both zones at the inner diameter of the second zone. In embodiments, each zone may be described as an even asphere, such that the zones are radially symmetric.

Each of the zones in the discontinuous multizonal surface 102 can be defined individually according to the coefficients of the lens equation above. For example, a spherical surface (e.g. zone 1) can be defined where all of the coefficients of the equation, except the curvature, are zero, and the aspheric surface can be defined where a number of the coefficients are nonzero. By way of example, the multizonal lens surface 102 can be described according to the coefficients of Table 2 below.

TABLE 2

Exemplary geometry of a multizonal lens surface.

| | Relative power | diameter | r | k | $a_4$ | $a_6$ | $a_8$ | $a_{10}$ | $a_{12}$ |
| --- | --- | --- | --- | --- | --- | --- | --- | --- | --- |
| Zone 1 | 2.3 D | 1 mm | 9.7 | 0 | 0 | 0 | 0 | 0 | 0 |
| Zone 2 | 0 D | 5 mm | 11.6 | −1.0 | −7.3E−04 | −9.3E−04 | 0 | 0 | 0 |

The radius of the first zone (R) can be related to the relative power (RP) according the equation 2, below, where $R_{post}$ is the radius of the posterior surface, d is the central thickness of the lens, $P_{base}$ the base power and $n_L$ and $n_m$ are the refractive index of the lens and the media, respectively. The radius of the second zone can be calculated so that in combination with that of the posterior surface, thickness and refractive index of the lens and surrounding media provide with the base power as defined in Table 2.

Equation for determining radius of curvature as a function of the relative power (RP)

$$R = \frac{1000}{n_L R_{post} \left( \frac{1000}{R_{post}} + \frac{P_{base} + RP}{n_L - nm} \right)} (n_L R_{post} + (n_L - nm)d) \quad \text{Equation 2}$$

Alternatively, the radius of the first zone can be calculated from the relative power (RP) and the radius of the second zone ($R_z$) from Equation 3, below:

Determining the radius of the first zone.

$$R = \frac{1000}{\frac{1000}{R_z} + \frac{RP}{n_L - n_m}} \quad \text{Equation 3}$$

The continuous power progressive lens surface 104, unlike the multizonal surface 102, is defined by a single aspheric equation that is configured to approximate elevations of the multizonal surface and can be described by Equation 1. Although the multizonal surface can be derived by merging the edges of the first and second zones (e.g., by matching an elevation of the outer perimeter of Zone 1 with an inner perimeter of Zone 2) so that a height profile is continuous from the central or optical axis of the lens to the outer periphery, the slope of the multizonal lens is not continuous, which causes the power profile to have a sharp discontinuity as well.

Table 3, below, describes the geometry of the exemplary continuous power progressive lens surface based on the multizonal lens surface described in Table 2, once fitted to a unique aspheric surface defining a continuous progressive lens surface.

TABLE 3

Geometry of an exemplary continuous power progressive lens surface.

| r | k | $a_4$ | $a_6$ | $a_8$ | $a_{10}$ | $a_{12}$ |
|---|---|---|---|---|---|---|
| 9.7 | 1.8E+00 | −1E−02 | 6E−03 | −2E−03 | 2E−04 | −1E−05 |

In FIG. 1, the multizonal lens 102 includes a first zone 108 defined by the first zone outer perimeter 106, and a second zone 112, which is defined between the first zone outer perimeter 106 and the lens periphery 110. In some cases, as illustrated in this example, the first zone 108 may be a spherical surface having a constant optical power from the center 122 of the lens 102 to the first zone outer perimeter 106. The second zone 112 can be an aspheric surface having a gradual change in the optical power from the first zone outer perimeter 106 to the lens periphery 110.

The structure of the continuous power progressive lens surface 104 differs from the multizonal surface 102 as follows, in accordance with embodiments. Instead of a stark boundary between first and second zones, a first region 116 blends continuously into a second region 120. A region boundary 114 is eliminated and the slope of the lens surface from the first region 116 to the second region 120 changes gradually over radial distance from the center 124 of the continuous power progressive lens surface 104 to the periphery 118. However, the aspheric equation defining the continuous power progressive lens surface 104 can approximate multiple optical regimes across the surface. For example, the first region 116 can approximate attributes of the spherical first zone 108, e.g. by providing an equivalent optical power across at least part of the first region 116. The second region 120 can likewise provide an optical power across at least a portion of the second region that is approximately equivalent to an optical power of the second zone 112.

Figure 2:
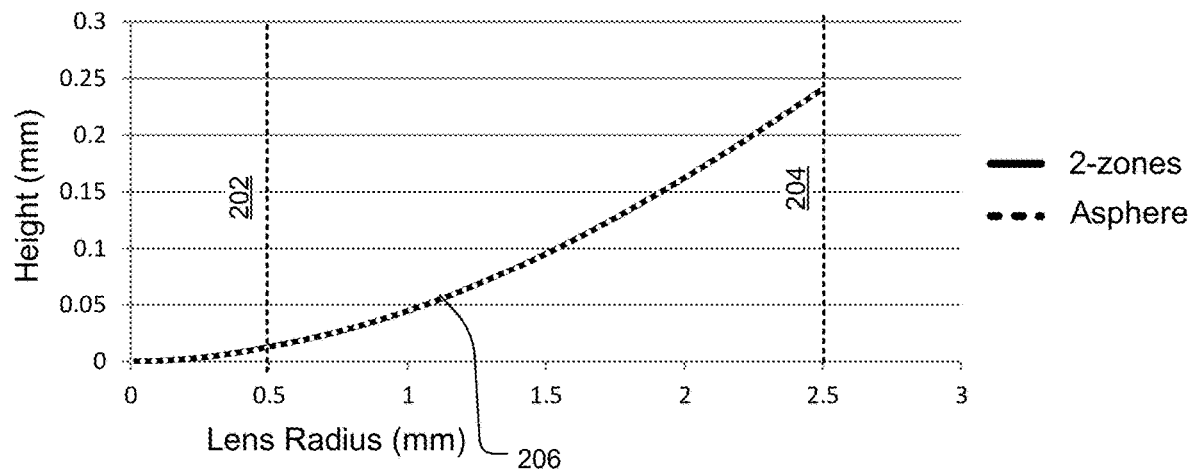
FIG. 2 illustrates elevation profiles of the multizonal surface and the analogous progressive power lens of FIG. 1.
Figure 3:
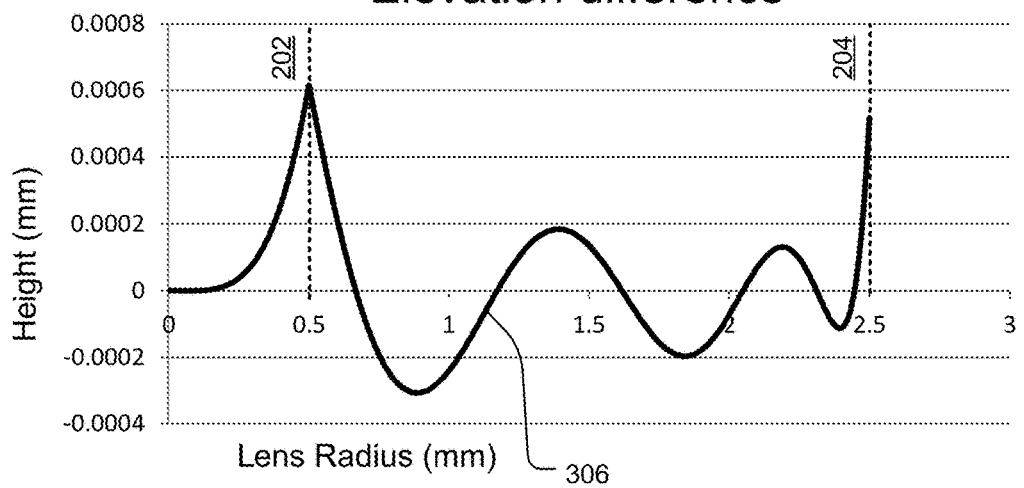
FIG. 3 illustrates a difference between the elevation profiles shown in FIG. 2 in more detail.

FIG. 2 shows an elevation profile 206 of the continuous power progressive lens surface 104 overlaid on the elevation profile of the multizonal lens 102 (FIG. 1), in accordance with embodiments. The continuous power progressive lens surface 104 appears similar to the multizonal lens 102 with subtle differences that are more readily visible by mapping the elevation difference 306 between the two lens surfaces, as shown in FIG. 3. The continuous power progressive lens surface 104 closely approximates the multizonal lens 102 where the elevation difference is zero, e.g., at a radial distance of zero (the lens center), and is most different from the multizonal lens near a first boundary 202 between the first and second zones, e.g. at a radial distance of 0.5 mm, where the smooth geometry of the continuous power progressive lens surface 104 differs from the discontinuous slope of the multizonal lens 102, and at an outer periphery 204.

Although the elevation differences between the multizonal surface 102 and the analogous continuous progressive lens surface 104 (FIG. 1) are subtle, the effects of the different elevation profiles may be more readily understood by referring to a comparison between the power profiles of the lenses.

Figure 4:
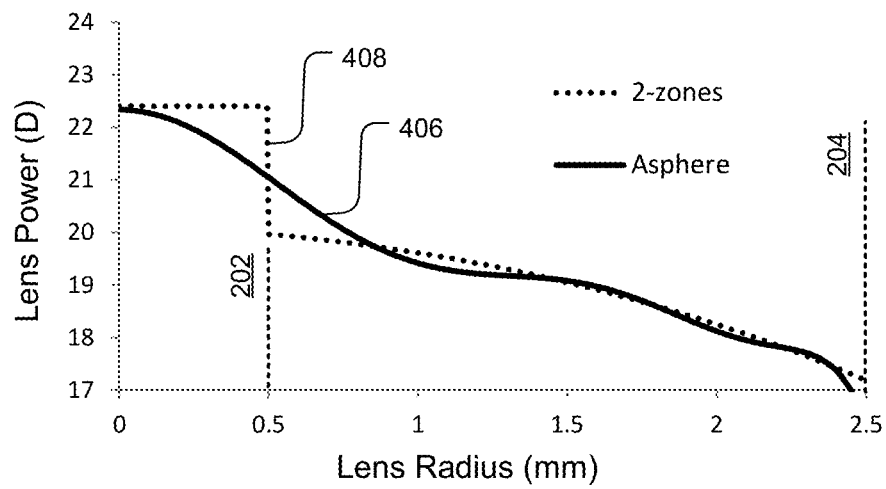
FIG. 4 illustrates power profiles of the multizonal surface and an analogous progressive power lens of FIG. 1.

FIG. 4 illustrates the multizonal power profile 408 of the multizonal surface 102 and the analogous continuous progressive power profile 406 of the continuous progressive lens surface 104 shown in FIG. 1. The multizonal surface (2-zones) is characterized by a constant optical power of greater than 22 diopters in Zone 1 from a radial distance of 0 with respect to the optical axis of the intraocular lens to a radial distance of 0.5 mm, which defines the outer perimeter 202 of the first zone. The optical power is discontinuous at the radial distance of 0.5 mm, and thereafter follows a diminishing power profile according to the aspheric surface of Zone 2. In the continuous progressive lens surface (asphere), the optical power at the lens center is approximately equal to the power of Zone 1. The power profile of the continuous progressive lens surface 406 (asphere) decreases without a discontinuity to approximate the optical power of Zone 2.

Figure 5:
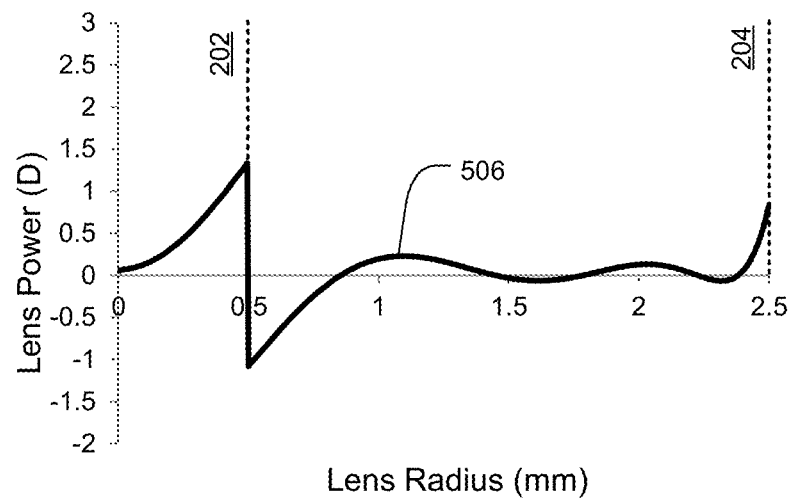
FIG. 5 illustrates a difference between the power profiles of the multizonal surface and an analogous progressive shown in FIG. 4.

FIG. 5 illustrates the difference in power profiles 506 between the multizonal surface 102 and the analogous continuous progressive lens surface 104 (FIG. 1) as shown in FIG. 4, in greater detail. The power profiles are most closely matched at the lens center (radial distance=0) and in a majority of the second region 120 (FIG. 1), with the greatest difference in power profiles near the power profile discontinuity at the first zone boundary 202.

Figure 6:
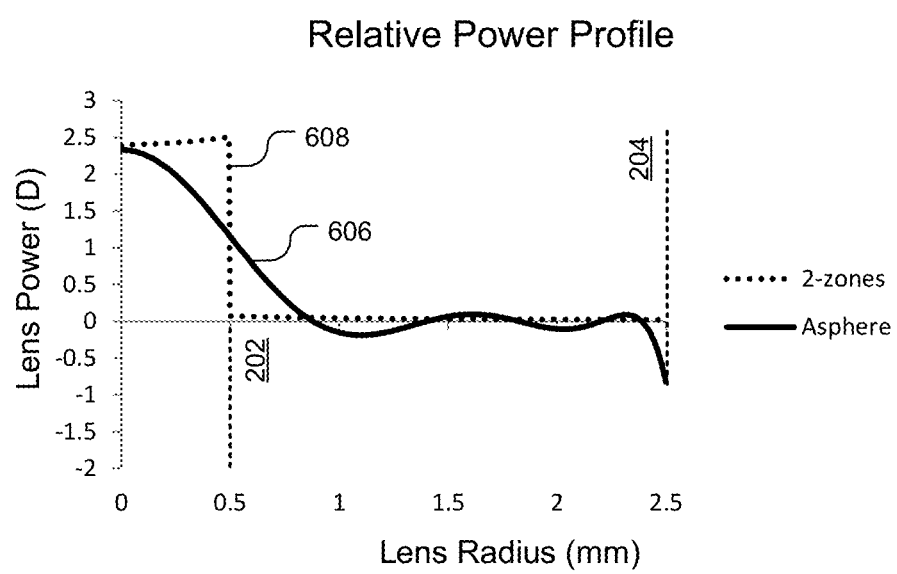
FIG. 6 illustrates the difference between the power profiles of the multizonal surface and an analogous progressive shown in FIG. 4 in terms of the relative power over the second zone.

By way of further example, FIG. 6 illustrates the power profile difference of a power progressive aspheric lens 606 and the 2-zonal surface 608, normalized with respect to a power profile of a standard aspheric monofocal surface. The 2-zonal lens power profile 608 and aspheric power progressive lens power profile 606 relate, respectively, to the 2-zone lens surface 102 and the analogous continuous progressive lens surface 104 shown in FIG. 1. FIG. 6 illustrates that the power profile of the continuous progressive lens surface differs from both a standard, monofocal aspheric profile and from a multizonal surface 102.

In various embodiments, the size of a central region of a continuous progressive lens surface can be increased, obtaining similar results to increasing the size of a central zone of a multizonal surface. For example, Table 4 below illustrates two different designs that have two zones, similar to the multizonal surface 102 (FIG. 1).

TABLE 4

Lens parameters of example lens surfaces A1 and A2

| Lens Design | Zone 1 (spherical) | | Zone 2 (aspheric) | |
|---|---|---|---|---|
| | Relative power | Extension (diameter) | Relative power | Extension (diameter) |
| A1 | 1.75 D | 1.5 mm | 0 D | Rest of lens |
| A2 | 1.75 D | 1.3 mm | 0 D | Rest of lens |

In lens designs A1 and A2 referenced above in Table 4, the central zone (Zone 1) is spherical and the peripheral zone (Zone 2) is aspheric. Zone 1 and 2 of designs A1 and A2 have the same geometry (same maximum relative power in the central zone (−1.75 D) and same base power in the peripheral zone (0 D)). However, the central zone has different extension (either 1.3 mm or 1.5 mm diameter). Table 5, below, describes the geometry of each zone for both designs, in terms of curvature and higher order aspheric terms. It should be noted that although both designs are based on the same geometrical parameters for defining the two zones (Table 5), the final designs differ (Table 6) because of the differences in the size of the central zone.

TABLE 5

Lens parameters of example lens surfaces A1 and A2

|    |        | r    | k       | $a_4$  | $a_6$  | $a_8$  | $a_{10}$ | $a_{12}$ |
|----|--------|------|---------|--------|--------|--------|----------|----------|
| A1 | Zone 1 | 10.1 | 0.0E+00 | 0E+00  | 0E+00  | 0E+00  | 0E+00    | 0E+00    |
|    | Zone 2 | 11.7 | 1.1E+00 | −7E−04 | −1E−05 | 0E+00  | 0E+00    | 0E+00    |
| A2 | Zone 1 | 10.1 | 0.0E+00 | 0E+00  | 0E+00  | 0E+00  | 0E+00    | 0E+00    |
|    | Zone 2 | 11.6 | 1.1E+00 | −7E−04 | −1E−04 | 0E+00  | 0E+00    | 0E+00    |

Table 6, below, describes the geometry of both designs A1 and A2 once fitted to a unique aspheric surface defining a continuous progressive lens surface.

TABLE 6

Geometry of the fitted aspheric surfaces generated from lenses A1 and A2

|    | r    | k       | $a_4$  | $a_6$  | $a_8$ | $a_{10}$ | $a_{12}$ |
|----|------|---------|--------|--------|-------|----------|----------|
| A1 | 9.9  | 6.5E−03 | −4E−03 | −1E−03 | 4E−04 | −9E−05   | 6E−06    |
| A2 | 10.0 | −6.0E−04| −5E−03 | 1E−03  | 6E−05 | −4E−05   | 3E−06    |

Varying the extension of the central region as described above before generating the continuous progressive lens surface can change the performance of the lens. For example, adjusting the extension of the central region can change the defocus performance of the lens.

Figure 7A:
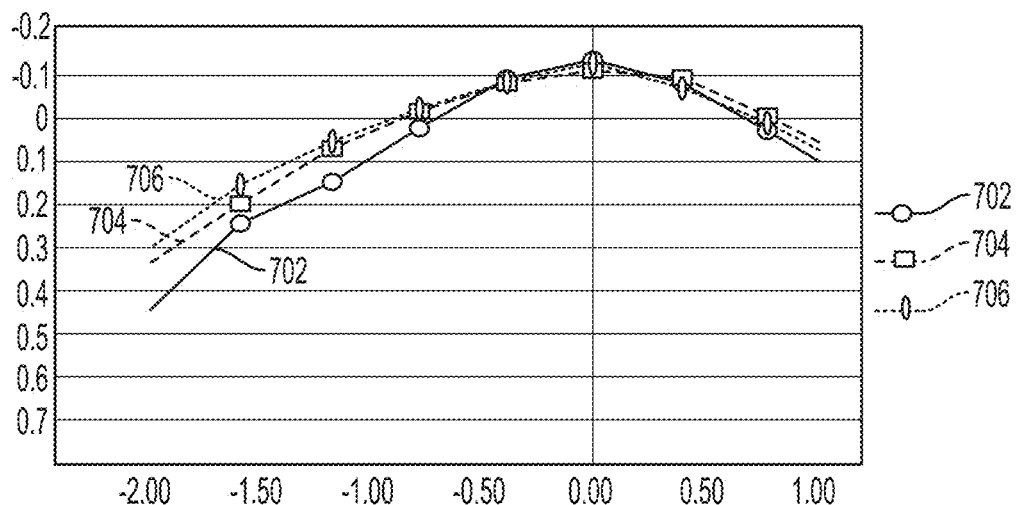
FIG. 7A shows the simulated visual acuity of three example lenses for a pupil size of 3 mm.
Figure 7B:
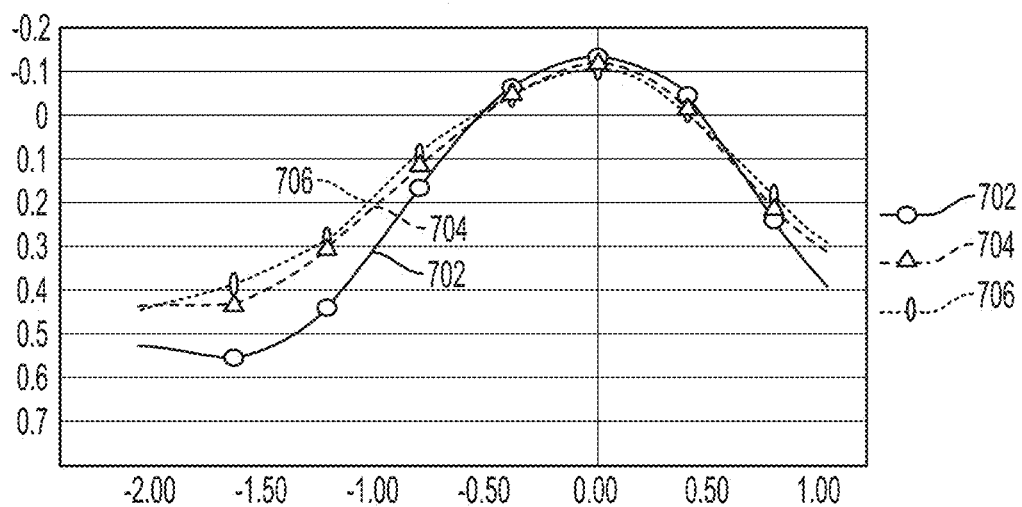
FIG. 7B shows the simulated VA of the example lenses of FIG. 7A for a pupil size of 5 mm.

By way of example, FIGS. 7A-B illustrate the simulated visual acuity of lenses A1 706 and A2 704, with an exemplary monofocal aspheric lens 702 for comparison purposes, for 3 mm and 5 mm pupil sizes respectively. Visual acuity is calculated according to methods described in U.S. patent application Ser. No. 14/878,294 entitled, "Apparatus, Systems and Methods for Improving Visual Outcomes for Psuedophakic Patient," which is hereby incorporated by reference. FIG. 7A shows the simulated visual acuity (VA) of the example lenses for a pupil size of 3 mm, and FIG. 7B shows the simulated VA of the example lenses for a pupil size of 5 mm.

FIGS. 7A-7B demonstrate that adding the central region (the region of the continuous progressive lens surface derived from Zone 1 of the multizonal surfaces) increases depth of focus. In particular, the depth of focus is increased over the monofocal model, as shown by the increased depth of focus of the continuous progressive lens curves 706, 704 (for A1 and A2, respectively) over the monofocal depth of focus curve 702 for the exemplary monofocal surface (FIGS. 7A, 7B). For the lens designs of FIGS. 7A-7B the depth of focus is increased with respect to that of the monofocal aspheric lens. The impact of the central zone size is also more readily apparent for the smaller pupil than for the larger pupil. FIGS. 7A-7B demonstrate that the best focus (defocus position with the best visual acuity) of the progressive lens A1 and A2 does not change with the pupil size.

Performance can also be modified by changing the asphericity of the continuous progressive lens surface near the periphery of the lens in an intraocular lens based on two zones. For example, Tables 6-8, below, illustrate aspects of another example of a multizonal lens surface and a continuous progressive lens surface derived therefrom. Table 7 describes the parameters of the third example surface A3. Table 8 describes the geometry of each zone of a multizonal surface conforming to the parameters of Table 7. As illustrated by Table 8, A3 only differs from A2 in the conic constant and higher order aspheric terms describing the second zone. The second zone of A3 resulted in a surface that induces negative spherical aberration, but does not fully compensate for that of the cornea. Table 9 describes the geometry of an aspheric surface defining a continuous progressive lens surface based on the multizonal surface described in Table 8.

TABLE 7

Lens parameters of the third example surface A3

| Lens Design | Zone 1 (spherical) | | Zone 2 (aspheric) | |
|---|---|---|---|---|
|  | Relative power | Extension (diameter) | Relative power | Extension (diameter) |
| A3 | 1.75 D | 1.30 mm | 0 D | Rest of lens |

TABLE 8

Geometry of the multizonal surface of lens A3

|    |        | r    | k       | $a_4$  | $a_6$  | $a_8$ | $a_{10}$ | $a_{12}$ |
|----|--------|------|---------|--------|--------|-------|----------|----------|
| A3 | Zone 1 | 10.1 | 0.0E+00 | 0E+00  | 0E+00  | 0E+00 | 0E+00    | 0E+00    |
|    | Zone 2 | 11.6 | 1.8E+00 | −6E−04 | −1E−05 | 0E+00 | 0E+00    | 0E+00    |

TABLE 9

Geometry of the fitted aspheric surface generated from lens A3

|    | r   | k       | $a_4$  | $a_6$ | $a_8$  | $a_{10}$ | $a_{12}$ |
|----|-----|---------|--------|-------|--------|----------|----------|
| A3 | 9.6 | 5.0E−03 | −1E−02 | 5E−03 | −1E−03 | 2E−04    | −8E−06   |

FIGS. 8A-8B demonstrate that changing the asphericity in the periphery does not significantly affect the optical performance (visual acuity) for smaller pupil sizes. Note that, in FIG. 8A, the A3 curve 802 does not differ significantly from the A2 curve 704. However, at larger pupil sizes, as shown in FIG. 8B, the A3 lens increases the depth of focus over the A2 lens. In particular, the depth of focus is further increased over the monofocal model, as shown by the increased depth of focus of the A3 lens curve 802 over the monofocal depth of focus curve 702 for the exemplary monofocal surface. A spherical aberration for the peripheral zone can be selected, and then the peripheral zone can be designed based on the amount of asphericity indicated.

Extended Depth of Focus

Embodiments herein disclosed also relate to lenses having a refractive aspheric profile that provides a continuous power progression to provide an extended depth of focus (EDF). The sag of power progressive designs herein disclosed is described by Equation 1. The power progression can be imposed on the anterior or on the posterior lens surface. Table 10 describes a range of values for the parameters describing power progressive refractive profiles on an anterior lens surface for a base lens power of 20 D. Furthermore, a power progressive surface may be applied to the posterior lens surface instead of, or in addition to, the anterior lens surface.

TABLE 10

Range of values for lens sag coefficients describing the power progression applied on an anterior side of an ophthalmic lens

|  | Lower limit | Upper limit |
|---|---|---|
| R | −8 | 12 |
| k | −5 | 7 |
| $a_4$ | −0.02 | 0 |
| $a_6$ | −0.003 | 0.01 |
| $a_8$ | −0.003 | 0.002 |
| $a_{10}$ | −0.0003 | 0.0003 |
| $a_{12}$ | −1.0E−04 | 1.0E−04 |

Figure 9:
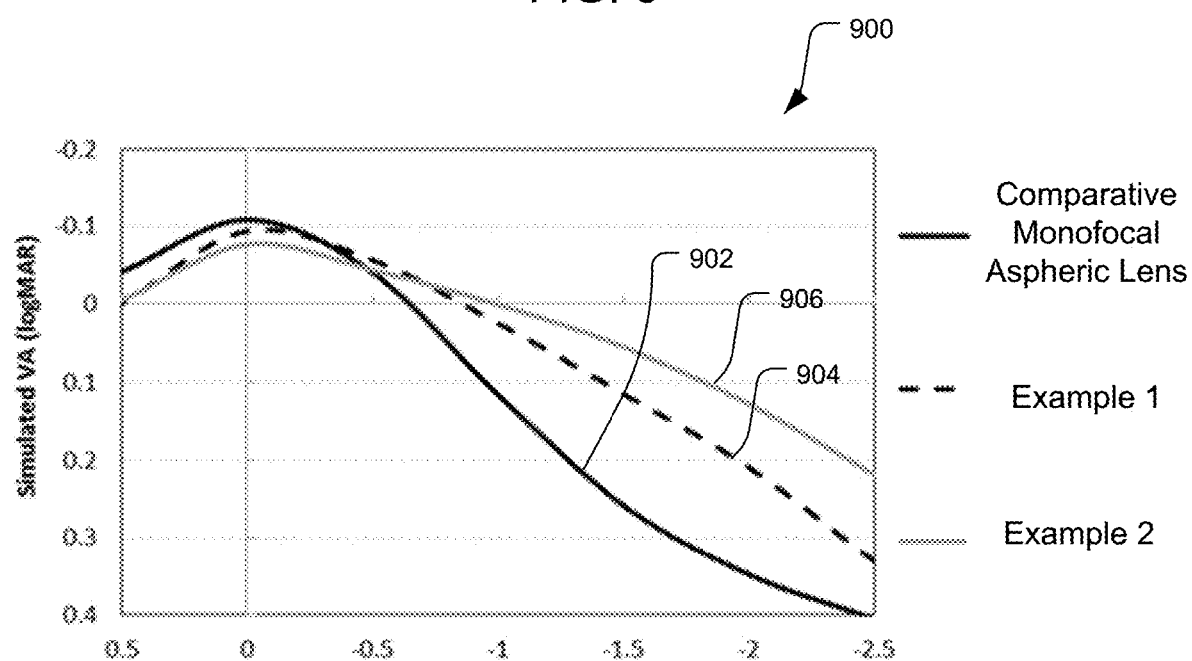
FIG. 9 shows a simulated VA for two example progressive power lenses with reference to a comparative monofocal aspheric lens.

By way of example, Table 11 describes the geometry of two progressive in power surfaces that provide EDF. FIG. 9 is a graphical illustration 900 that shows the simulated visual acuity imparted by the lenses described in Table 11. As shown, both lenses Example 1 (904) and Example 2 (906) provide high visual acuity compared to a comparative, monofocal aspheric lens 902 throughout an extended focal depth. This visual acuity data demonstrates that the lenses impart extended depth of focus with respect to a monofocal IOL.

TABLE 11

Geometry of the fitted aspheric surfaces of Example Lenses 1 and 2 (FIG. 9)

|  | r | k | $a_4$ | $a_6$ | $a_8$ | $a_{10}$ | $a_{12}$ |
|---|---|---|---|---|---|---|---|
| Example 1 | 9.0E+00 | −4.8E−03 | −1.3E−02 | 5.8E−03 | −1.4E−03 | 1.7E−04 | −8.0E−06 |
| Example 2 | 9.7E+00 | −5.5E−01 | −1.2E−02 | 5.7E−03 | −1.4E−03 | 1.7E−04 | −8.1E−06 |

The range of coefficients described in Table 11 are applicable for refractive power progressive profiles with a base power of 20 D. For any given design aspheric progressive in power design, the full range of IOL powers can be expanded. By way of example, Table 12 shows a range of coefficient values describing an aspheric power progressive surface applied to an anterior side of an ophthalmic lens for a range of base powers between approximately 0 D and 50 D. In specific embodiments, the range of base powers can be between 0 D and 50 D, or preferably between 0 D and 40 D, or more preferably from about 5 D to about 34 D, from about 10 D to 30 D, or from 16 D to 28 D.

TABLE 12

Range of values for lens sag coefficients describing a power progression applied on an anterior side of an ophthalmic lens

|  | Lower limit | Upper limit |
|---|---|---|
| R | 4 | 29 |
| k | −3 | 13 |
| $a_4$ | −0.02 | 0 |
| $a_6$ | 0 | 0.01 |
| $a_8$ | −0.003 | 0 |
| $a_{10}$ | 0 | 0.0003 |
| $a_{12}$ | −1.0E−04 | 0 |

Figure 10:
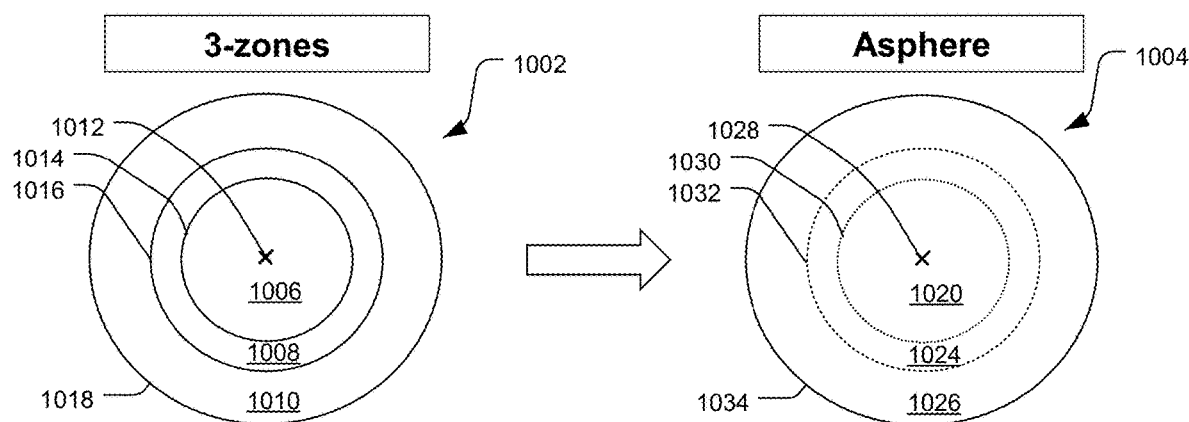
FIG. 10 illustrates a three-zone multizonal surface and an analogous progressive power lens based on the multizonal surface in a front view, in accordance with embodiments.

Exemplary Intraocular Lens Shapes Approximating 3-Zone Surface:

FIG. 10 illustrates a 3-zone multizonal surface 1002 and an analogous, continuous power progressive lens surface 1004 based on the multizonal surface in a front view, in accordance with embodiments. Unlike the two-zone multizonal surface 102 of FIG. 1, the surface 1002 includes three concentric lens surfaces defining a first zone 1006 that is concentric and radially symmetric about an optical axis 1012, a second zone 1008 that is concentric with the first zone and also radially symmetric about the optical axis, and a third zone 1010 that is concentric with the first and second zones, and radially symmetric about the optical axis. The first and second zones 1006, 1008 meet at a first zone boundary 1014. The second and third zones 1008, 1010 meet at a second zone boundary 1016. The third zone 1010 extends to the lens periphery 1018.

The continuous power progressive lens surface 1004 based on the above-described multizonal lens surface is defined by a single aspheric equation based on Equation 1, described above. The continuous power progressive lens surface 1004 can be described in terms of regions that approximate elevations of the multizonal surface. For example, a first region 1020, a second region 1024, and a third region 1026 are concentric about the optical axis 1028 and radially symmetric. The first, second, and third regions 1020, 1024, 1026 can be nominally defined by the first region boundary 1030, second region boundary 1032, and lens periphery 1034. However, and unlike the multizonal surface 1002 from which the continuous power progressive lens surface is derived, there are no discontinuities in the slope of the elevation profile of the continuous power progressive lens surface between the lens center 1028 and periphery 1034.

Varying Central Zone Relative Power in Three Zones:

Implementing designs based on three or more zones can provide for improved depth of focus at various distances, in accordance with embodiments. For example, Tables 13-15 below describe attributes of designs having three zones or regions. Table 13 describes the parameters of various exemplary three-zone multizonal lens surfaces. Table 14 describes the geometry of each multizonal surface conforming to the parameters of Table 13. Table 15 describes the geometry of each aspheric surface defining a continuous progressive lens surface based on the multizonal surfaces described in Table 14.

TABLE 13

Parameters of exemplary 3-zone multizonal lens surfaces.

| | Zone 1 | | Zone 2 | | Zone 3 | |
|---|---|---|---|---|---|---|
| | Relative Power | Extension (Diameter) | Relative Power | Extension (Diameter) | Relative Power | Extension (Diameter) |
| H10 | 2.75 D | 0.75 mm | 1.75 | 1.5 mm | 0 | Rest |
| I10 | 1.75 D | 0.75 mm | 0.75 | 1.5 mm | 0 | Rest |
| J10 | 2.25 D | 0.75 mm | 1.25 | 1.5 mm | 0 | Rest |

In all cases above, the middle zone has a positive relative power over the peripheral zone (zone 3) different from the base power of the lens, and the central zone (zone 1) has a positive relative power that is one diopter higher than the intermediate zone (zone 2). All zones have the same extension for all the designs, 0.75 mm (diameter) and 1.5 mm for the first and second zones, respectively. As described above for the 2-zone cases, each individual zone can be described according to Equation 1, as described below according to Table 14.

TABLE 14

Lens parameters of example lens surfaces H10, I10, J10 before fitting.

| | | r | k | $a_4$ | $a_6$ | $a_8$ | $a_{10}$ | $a_{12}$ |
|---|---|---|---|---|---|---|---|---|
| H10 | zone 1 | 9.4 | 0 | 0 | 0 | 0 | 0 | 0 |
| | zone 2 | 10.8 | 0 | 0 | 0 | 0 | 0 | 0 |
| | zone 3 | 11.6 | 1.1 | −7E−04 | −1E−05 | 0 | 0 | 0 |
| I10 | zone 1 | 10.1 | 0 | 0 | 0 | 0 | 0 | 0 |
| | zone 2 | 10.9 | 0 | 0 | 0 | 0 | 0 | 0 |
| | zone 3 | 11.6 | 1.1 | −7.2E−04 | −1E−05 | 0 | 0 | 0 |
| J10 | zone 1 | 9.7 | 0 | 0 | 0 | 0 | 0 | 0 |
| | zone 2 | 10.5 | 0 | 0 | 0 | 0 | 0 | 0 |
| | zone 3 | 11.6 | 1.1 | −7E−04 | −1E−05 | 0 | 0 | 0 |

Table 15, below, describes the geometry of power progressive lens surface designs H10, I10, and J10 once fitted to a unique aspheric surface defining a continuous power progressive lens surface.

TABLE 15

Geometry of the fitted aspheric surfaces generated for lenses H10, I10, J10.

| | r | k | $a_4$ | $a_6$ | $a_8$ | $a_{10}$ | $a_{12}$ |
|---|---|---|---|---|---|---|---|
| H10 | 9.0 | 4.5E−03 | −1E−03 | 6E−03 | −1E−03 | 2E−04 | −8E−06 |
| I10 | 10.4 | 8.9E−03 | −4E−03 | 5E−04 | 1E−04 | −4E−05 | 3E−06 |
| J10 | 9.8 | −5.1E−03 | −7E−03 | 2E−03 | −3E−04 | 7E−06 | 7E−07 |

Figure 11A:
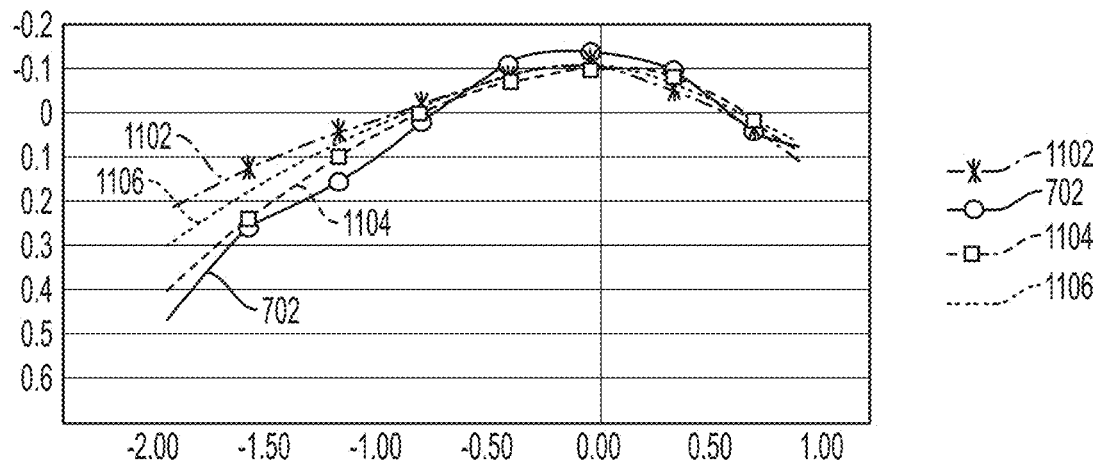
FIGS. 11A-11B show the simulated visual acuity two additional progressive power lens surfaces having varying relative powers in the central region respect to the base power of the lens, in comparison to example lenses shown in FIGS. 7A-7B, for pupil sizes of 3 mm and 5 mm, respectively.
Figure 11B:
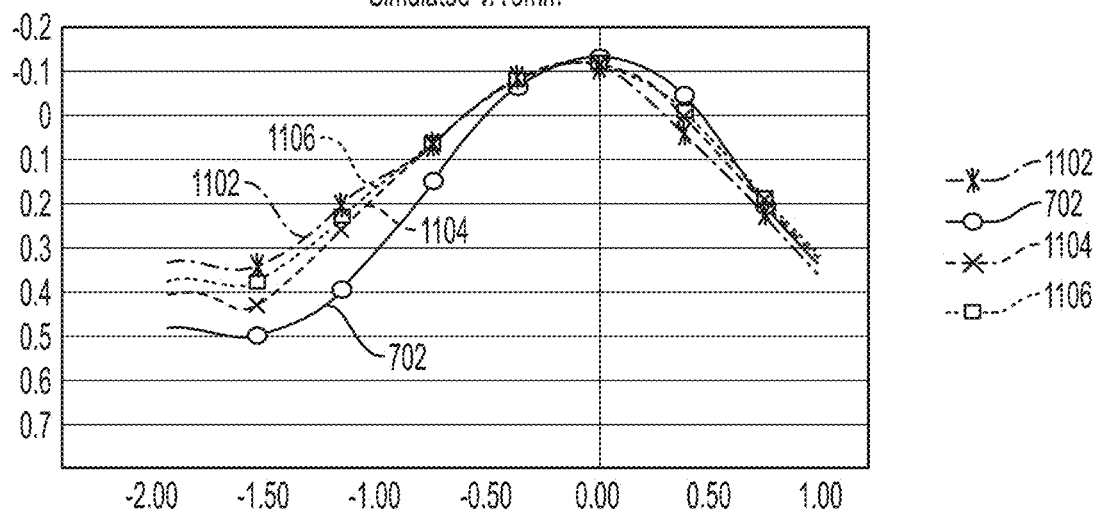

Varying the relative power of the central zone and intermediate zone with respect the base power of the peripheral zone can change the performance of the continuous power progressive lens surface resulting of the fitting, as shown in FIGS. 11A-11B.

By way of example, FIGS. 11A-B illustrate the simulated visual acuity of lenses H10, I10, and J10, with the exemplary monofocal aspheric lens 702 for comparison purposes, for 3 mm and 5 mm pupil sizes respectively. FIG. 11A shows the simulated visual acuity (VA) of the example lenses for a pupil size of 3 mm, and FIG. 11B shows the simulated VA of the example lenses for a pupil size of 5 mm.

FIGS. 11A-11B demonstrate that a more positive relative power at the central region increases depth of focus of the continuous power progressive lens surface resulting of the fitting. In particular, the depth of focus is increased over the monofocal model, as shown by the increased depth of focus of the continuous progressive lens curves 1102, 1104, and 1106 (for H10, I10, and J10, respectively) over the monofocal depth of focus curve 702 for the exemplary monofocal surface. The impact of the central zone positive power respect to the basic power is also more readily apparent for the smaller pupil than for the larger pupil. It is also possible to change the behavior of the continuous power progressive lens surface resulting of the fitting by changing the power in the outer zone of the initial multizonal design.

Varying Asphericity in the Periphery:

Changing the asphericity in the periphery can also allow for either increasing the depth of focus for large pupil sizes (i.e. when inducing more positive spherical aberration) or improving distance image quality. For example, Tables 16-17 below describe attributes of designs having three zones or regions, with varying degrees of peripheral asphericity.

Table 16 describes the parameters of exemplary three-zone multizonal lens surfaces with varying peripheral asphericity. The designs are ordered by decreasing spherical aberration at zone 3.

TABLE 16

Parameters of 3-zone multizonal lens surfaces with varying spherical aberration.

| | Zone 1 | | Zone 2 | | Zone 3 | | |
|---|---|---|---|---|---|---|---|
| | Relative Power | Extension (Diameter) | Relative Power | Extension (Diameter) | Relative Power | Extension (Diameter) | z12 |
| H3 | 2.75 D | 0.75 mm | 1.75 D | 1.5 mm | 0 | rest | +0.11 |
| H8 | 2.75 D | 0.75 mm | 1.75 D | 1.5 mm | 0 | rest | 0 |
| H9 | 2.75 D | 0.75 mm | 1.75 D | 1.5 mm | 0 | rest | −0.135 |
| H10 | 2.75 D | 0.75 mm | 1.75 D | 1.5 mm | 0 | rest | −0.2 |
| H7 | 2.75 D | 0.75 mm | 1.75 D | 1.5 mm | 0 | rest | −0.27 |

Table 17, below, describes the geometry of the designs of Table 16 once fitted to a unique aspheric surface defining a continuous power progressive lens surface.

TABLE 17

Geometry of fitted aspheric surfaces generated for lenses H3, H8, H9, H10, and H7

| | r | k | $a_4$ | $a_6$ | $a_8$ | $a_{10}$ | $a_{12}$ |
|---|---|---|---|---|---|---|---|
| H3 | 9.1 | −1.3E−02 | −1E−02 | 6E−03 | −1E−03 | 2E−04 | −8E−06 |
| H8 | 9.1 | −1.6E−02 | −1E−02 | 6E−03 | −1E−03 | 2E−04 | −8E−06 |
| H9 | 9.1 | −9.6E−03 | −1E−02 | 6E−03 | −1E−03 | 2E−04 | −8E−06 |

TABLE 17-continued

Geometry of fitted aspheric surfaces generated for lenses
H3, H8, H9, H10, and H7

| | r | k | $a_4$ | $a_6$ | $a_8$ | $a_{10}$ | $a_{12}$ |
|---|---|---|---|---|---|---|---|
| H10 | 9.0 | 4.5E–03 | –1E–02 | 6E–03 | –1E–03 | 2E–04 | –8E–06 |
| H7 | 9.0 | –4.8E–03 | –1E–02 | 6E–03 | –1E–03 | 2E–04 | –8E–06 |

Changing the asphericity in the periphery of the initial multizonal surface can improve the depth of focus for larger pupils (i.e., by inducing more positive spherical aberration) of the continuous power progressive lens surface resulting of the fitting, and can also improve distance image quality (i.e., by inducing a larger amount of negative spherical aberration).

Figure 12A:
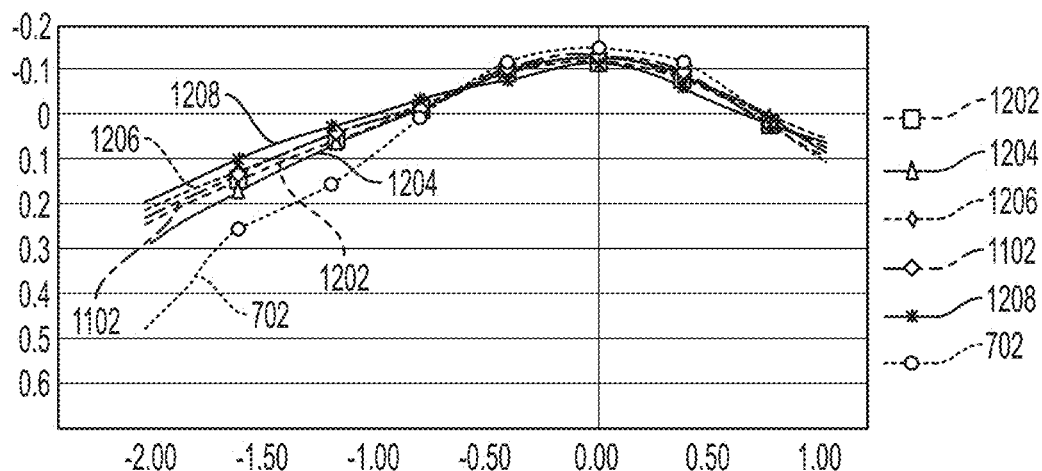
FIGS. 12A-12B show the simulated visual acuity of additional progressive power lens surfaces having varying asphericity in their periphery regions, in comparison to example lenses shown in FIGS. 7A-7B and 11A-11B, for pupil sizes of 3 mm and 5 mm, respectively.
Figure 12B:
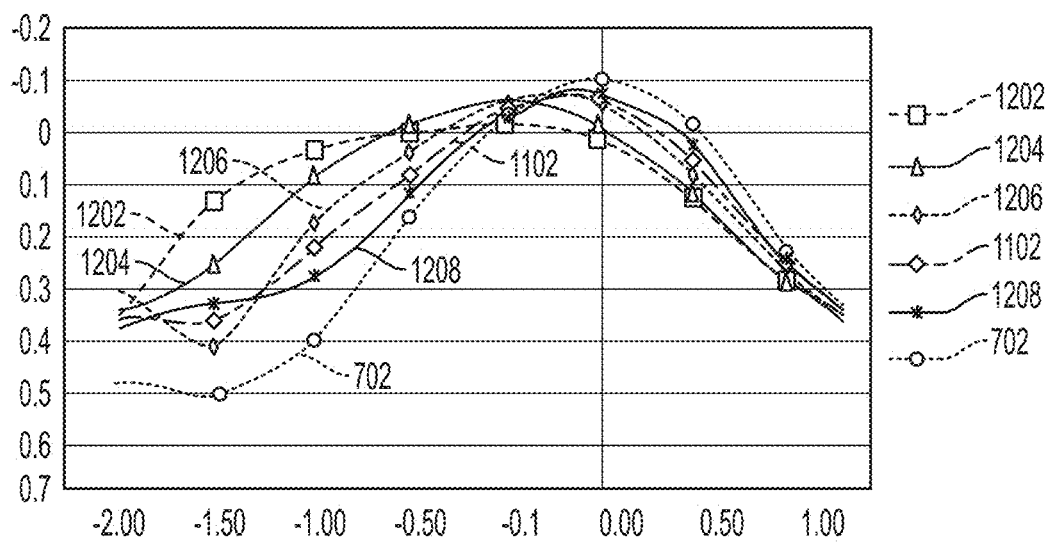

By way of example, FIGS. 12A-B demonstrate the effects of changing spherical aberration at the periphery of the initial multizonal surface on the simulated visual acuity of the continuous power progressive lens surface resulting of the fitting described in Tables 16 and 17, along with the exemplary monofocal aspheric lens 702 for comparison purposes. Note that the H10 curve 1102 for lens H10 is repeated from FIGS. 11A-B. FIG. 12A shows the simulated visual acuity (VA) of the example lenses for a pupil size of 3 mm, and FIG. 12B shows the simulated VA of the example lenses for a pupil size of 5 mm.

FIGS. 12A-12B demonstrate that all five continuous power progressive lens surface lenses display an increased depth of focus over the monofocal model, as shown by the increased depth of focus of the continuous progressive lens curves 1202, 1204, 1206, 1102, and 1208 (for H3, H8, H9, H10, and H7, respectively) over the monofocal depth of focus curve 702 for the exemplary monofocal surface. The impact of changing the asphericity is more readily apparent for the larger pupil than for the smaller pupil, as illustrated by the greater spread between the curves in FIG. 12B. Note that the H3 curve 1202 provides a particularly large depth of focus compared to the lenses with negative or zero perimeter spherical aberration on the initial multizonal zone. Conversely, the H7 curve 1208, illustrative of an intraocular lens with a particularly negative spherical aberration, provides a comparatively high distance image quality. By selecting the spherical aberration in the peripheral area, an intraocular lens can be tuned to balance distance visual quality and depth of focus so as to suit a patient with a particular visual need or a lifestyle preference, e.g. a patient who prefers to prioritize distance vision, intermediate vision, or near vision.

Figure 13:
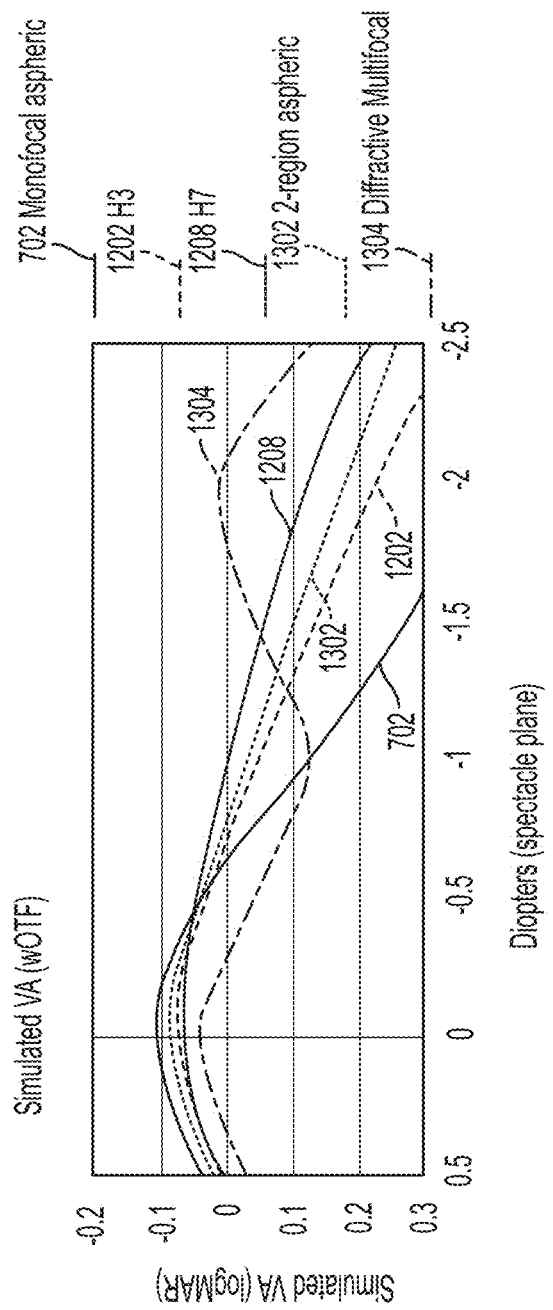
FIG. 13 illustrates simulated visual acuities of a various lenses including a monofocal lens, a multifocal lens, and three power progressive lens surfaces.

FIG. 13 illustrates the simulated visual acuity of various lenses with respect to the optical power. Exemplary curves shown include a reference aspheric monofocal 702, two of the three-region power progressive lens surfaces 1202 and 1208 (referring to lens surfaces H3 and H7 described above with reference to Tables 16-17 and FIGS. 12A-12B), a 2-region aspheric power progressive lens surface 1302, and an exemplary standard diffractive multifocal lens 1304.

FIG. 13 demonstrates improved optical performance of power progressive lenses 1202, 1208, 1302, and a diffractive multifocal lens 1304 over the monofocal aspheric lens 702 in terms of depth of focus for a pupil size of 3 mm. Additionally, performance at intermediate distances is improved in the fitted, aspheric power progressive lens surfaces 1202, 1208, and 1302 over the multifocal lens 1304. The visual acuity at far and intermediate distances for the multifocal lens 1304 is shown to be significantly lower than the visual acuity for the aspheric multifocal power progressive lenses.

Figure 14A:
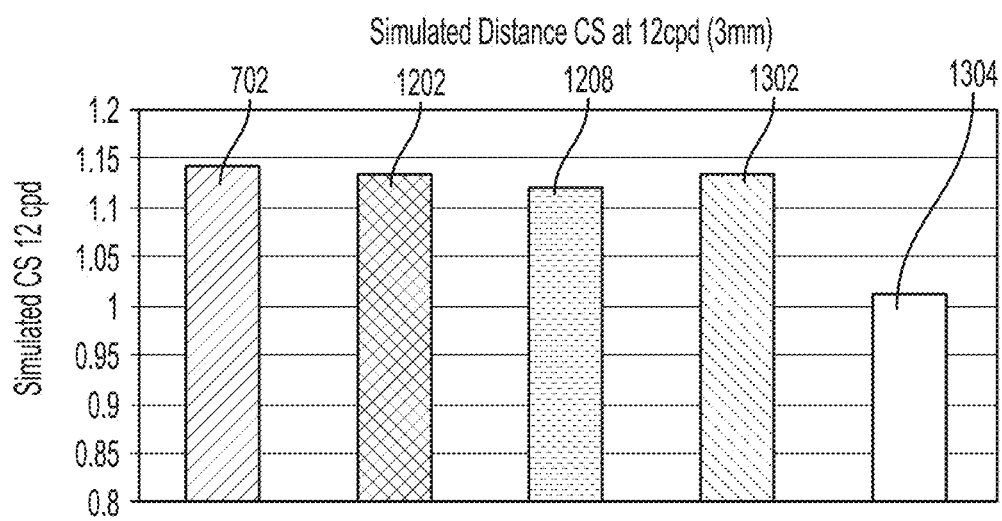
FIGS. 14A-14B illustrate simulated contrast sensitivity of the various lenses of FIG. 13 for a 3 mm pupil and 5 mm pupil, respectively.
Figure 14B:
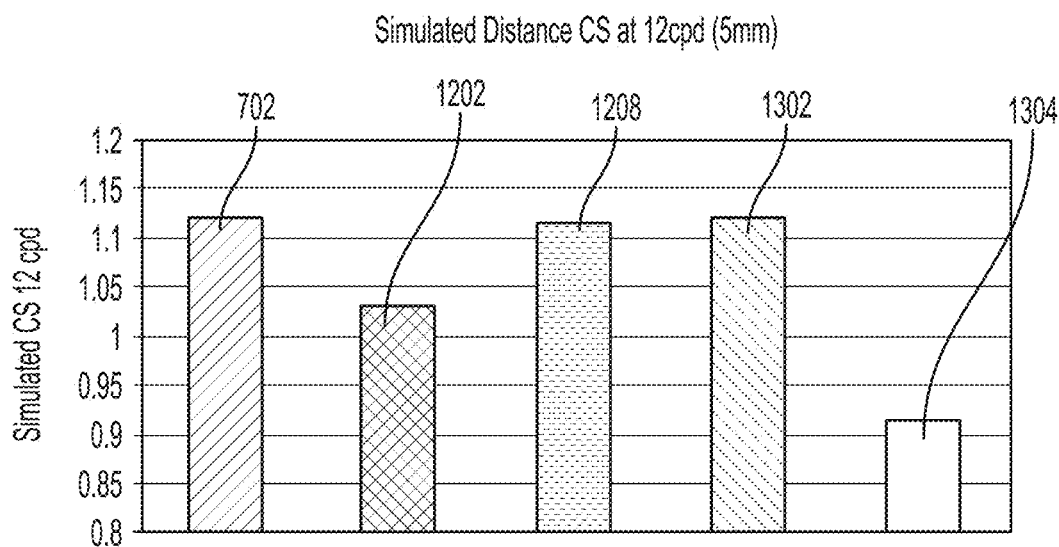

FIGS. 14A and 14B illustrate the simulated contrast sensitivity at 12 cycles per degree (cpd) for each of the lenses described above with respect to FIG. 13, for a 3 mm pupil and 5 mm pupil, respectively. FIG. 14A demonstrates that comparable distance contrast sensitivity is obtained between the example monofocal aspheric lens 702 and the aspheric power progressive lenses 1202, 1208, 1302, and 1304, while the standard diffractive multifocal lens 1304 provides less contrast sensitivity, for 3 mm pupils. FIG. 14B demonstrates that the effect of lens selection is greater for large (5 mm) pupil sizes, with the standard diffractive multifocal lens 1304 providing significantly less contrast sensitivity.

Figure 15A:
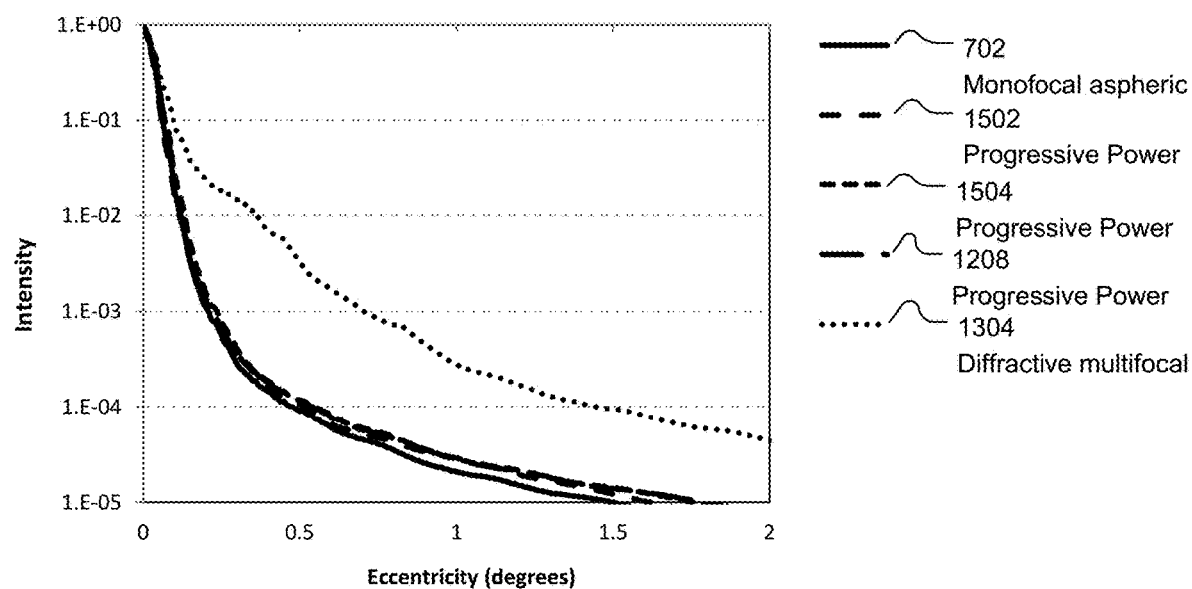
FIG. 15A illustrates the intensity of refractive artifacts produced by a selection of progressive power lens surfaces compared to an aspheric monofocal lens surface and diffractive multifocal lens surface.
Figure 15B:
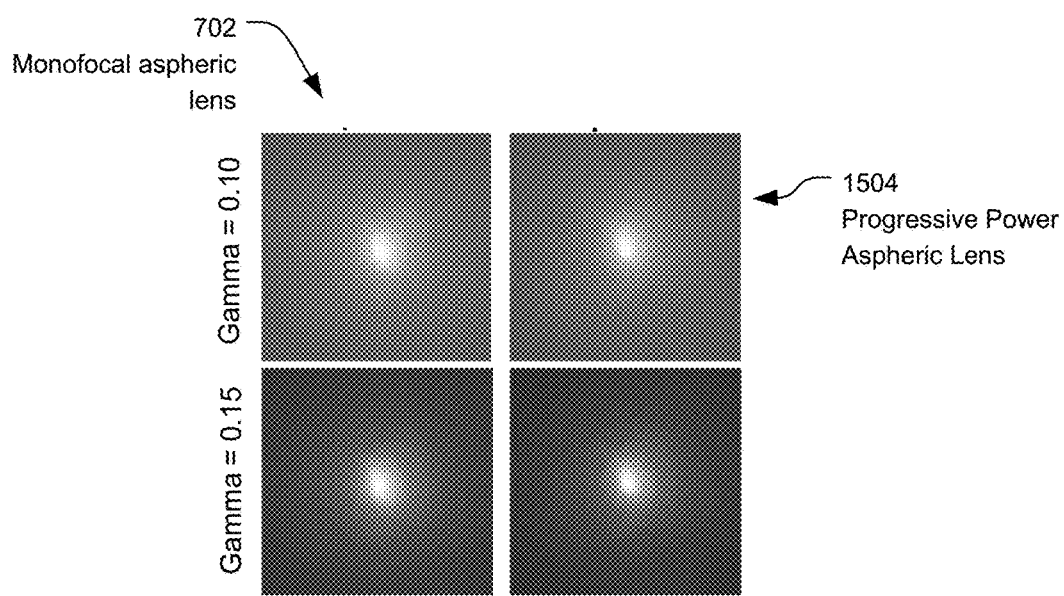
FIG. 15B shows a comparison of halos associated with a progressive power lens surface and an aspheric monofocal lens surface.

FIGS. 15A and 15B illustrate the pre-clinical dysphotopsia performance for various lenses. FIG. 15A shows the normalized light intensity exhibited through the example lenses as a function of visual angle. The reference monofocal aspheric lens 702 exhibits low intensity levels around the main image, while the example standard diffractive multifocal lens 1204 exhibits relatively high intensity levels for different eccentricities. FIG. 15A shows that three aspheric power progressive lenses 1502, 1504, and 1208 (H10 described in Tables 11-12) exhibit similar halo and glare performance (same light intensity distribution at various visual angles) than the monofocal aspheric lens 702. FIG. 15B shows the actual images on which the numerical data at FIG. 15A are based, showing intensity measurements of the reference aspheric monofocal lens 702 and the aspheric power-progressive lens 1504. These comparisons demonstrate that the fitted aspheric power-progressive lens designs display significantly reduced dysphotopsia effects compared to traditional multifocal lenses.

Power Progressive Lenses with Extended Depth of Focus (EDF)

Embodiments herein disclosed also relate to lenses having a refractive aspheric profile that provides a continuous power progression to extend depth of focus (EDF) in combination with diffractive profiles. Power progressive refractive profiles can be defined according to Equation 1.

Figure 16:
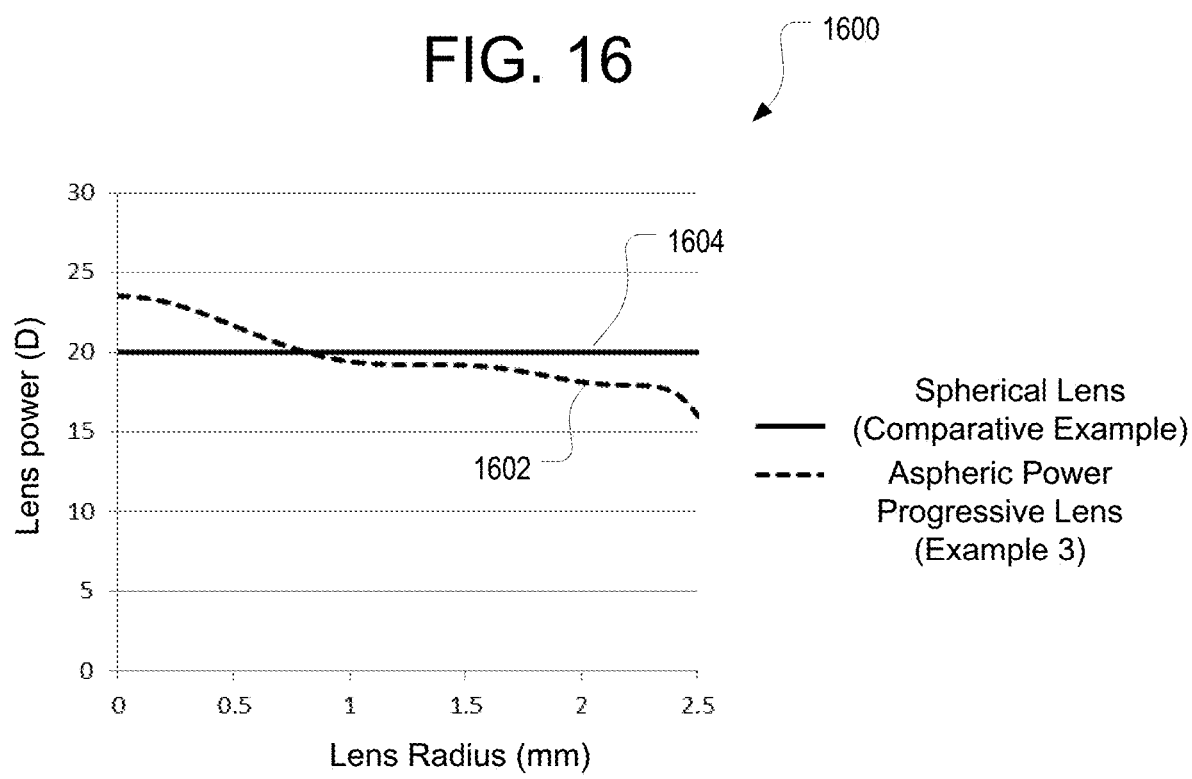
FIG. 16 illustrates the power profile of a refractive power-progressive lens compared to a spherical lens power profile.

By way of example, FIG. 16 compares the power profile of a power-progressive, aspheric EDF lens 1602 to that of a monofocal spherical lens (spherical lens) 1604. The power progression of the exemplary lens Example 3 in FIG. 1 is created by a higher order asphere that is positioned in the posterior IOL optic. The anterior IOL optic is also aspheric and completely compensates for average corneal spherical aberration. The profile is described by Equation 1 in combination with the coefficients of Table 18.

TABLE 18

Coefficients describing the power progressive aspheric
lens surface Example 3 as applied in a posterior side
of an ophthalmic lens

| R | k | $a_4$ | $a_6$ | $a_8$ | $a_{10}$ | $a_{12}$ |
|---|---|---|---|---|---|---|
| –12.9 | –5.3E–01 | 2E–02 | –9E–03 | 2E–03 | –3E–04 | 2E–05 |

FIG. 16 shows that, while the spherical lens has a continuous power, the higher order aspheric EDF profile determines a smooth power progression from the center to the periphery. Due to the continuity of power progression, there are no zones in the lens. Therefore, the lens appears visually identical to a monofocal IOL when visually inspected. Because the power profile is different at any radial point of the lens surface, the refractive aspheric profile substantially differs from either spherical or zonal power refractive profiles.

Figure 17:
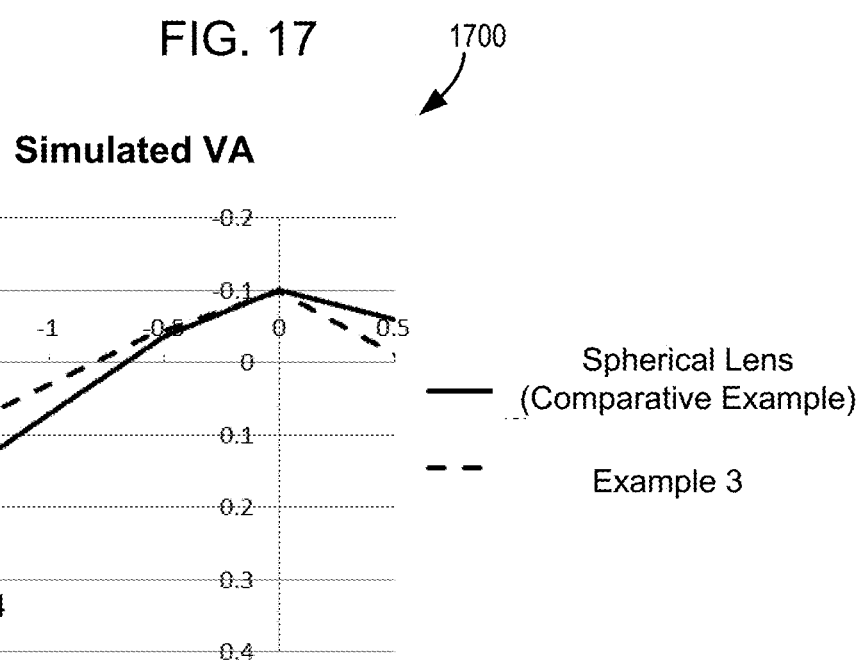
FIG. 17 shows simulated VA of an example of a refractive, power progressive EDF lens with reference to the simulated VA of a spherical lens.

FIG. 17 illustrates visual acuity by way of simulated defocus curves provided by the higher order aspheric profile of Example 3 (1602) and by the comparative example spherical lens 1604, whose power profiles have been shown in FIG. 16. FIG. 17 shows that the progressive power profile results in an extended depth of focus as compared to the spherical lens. The simulated visual acuity performance does not exhibit a bimodal performance, indicating that the continuous power profile effectively extends depth of focus.

Table 19 describes a range of values for the parameters of a power progressive refractive profile positioned on the posterior lens surface for a lens with a base power between 18 D and 20 D. These ranges are applicable when the anterior IOL lens surface is also aspheric and compensates for corneal spherical aberration. According to Table 19, a power progressive refractive profile with the features described herein has a posterior radius between about 11 and 18 mm.

TABLE 19

Range of values for coefficients describing the power progressive refractive profile applied to the posterior surface of an IOL for base powers between 18 D and 20 D

|  | Lower limit | Upper limit |
|---|---|---|
| R | −18 | −11 |
| k | −1 | 0.1 |
| $a_4$ | 0 | 0.05 |
| $a_6$ | −0.05 | 0 |
| $a_8$ | 0 | 0.01 |
| $a_{10}$ | −0.01 | 0 |
| $a_{12}$ | 0 | 0.0001 |

Figure 18:
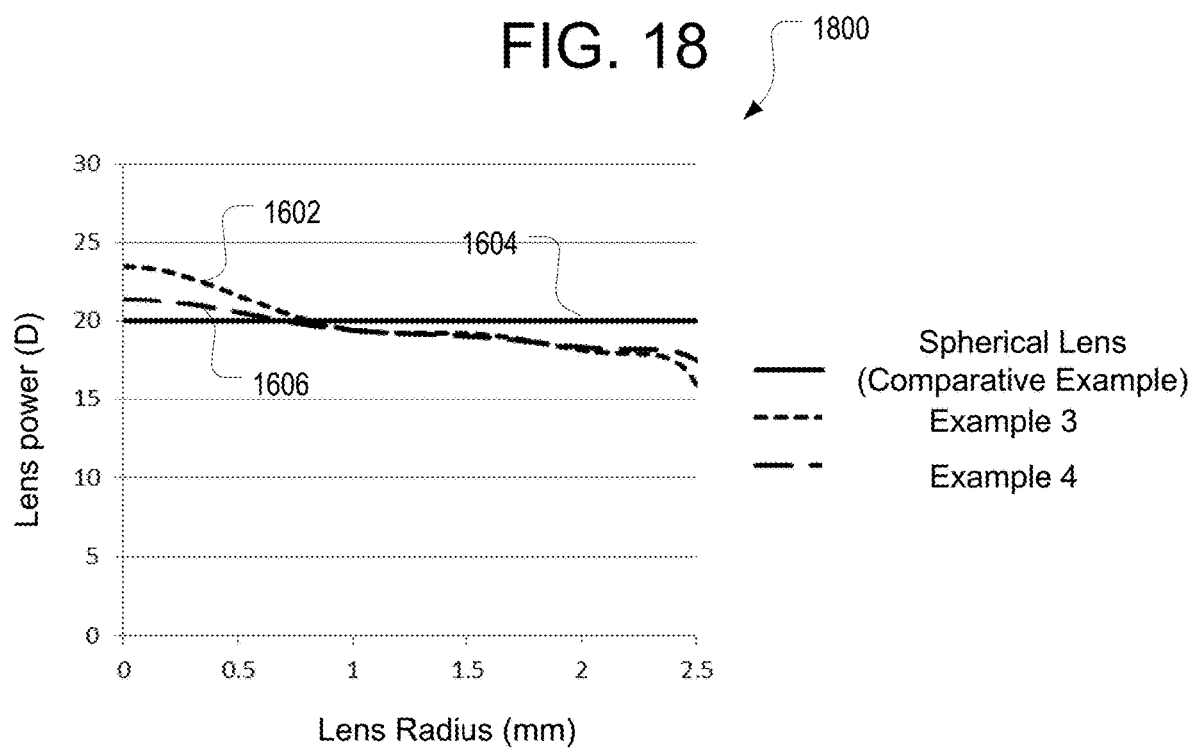
FIG. 18 illustrates power profiles of two example refractive power progressive lenses having different power profiles, with reference to a spherical lens power profile.

By way of example, FIG. 18 compares the power profile of a comparative monofocal spherical lens 1604 to that of two aspheric EDF designs, Example 3 (1602) as described by Table 18 and Example 4 (1606), whose coefficients are provided in Table 20, below. FIG. 18 shows that both aspheric EDF designs provide a smooth power progression from the center to the periphery, and providing a more pronounced power progression for Example 3 than for Example 4. The coefficients describing both Example 3 and Example 4 are within the range of values shown in Table 19. It should be noted that the smaller in absolute value the radius of the aspheric design, the steeper the power progression, as illustrated by the example provided in FIG. 18.

TABLE 20

Coefficients describing the power progressive lens surface applied to the posterior side of the lens of Example 4

| Design | R | k | $a_4$ | $a_6$ | $a_8$ | $a_{10}$ | $a_{12}$ |
|---|---|---|---|---|---|---|---|
| Example 4 | −16.3 | −8.1E−02 | 7E−03 | −4E−03 | 1E−03 | −1E−04 | 7E−06 |

The ranges of coefficients described in Table 19 are applicable for refractive power profiles with a base power between 18 D and 20 D. For a given aspheric design, the range of base IOL powers can be expanded. It is possible to create the full range of base powers of a given refractive EDF profile with a determined performance. For example, the design 1602 has a base power between 18 D and 20 D and defines a determined power progression. The same relative power progression can be obtained for different base powers. Table 21 contains the coefficients that define the full range of base IOL powers with the relative power progression that defines the design 1604. Table 21 shows the ranges of coefficients describing a power progressive lens surface similar to Example 3 for a range of base powers between approximately 0 D and 50 D, or preferably between 0 D and 40 D, or more preferably from about 5 D to about 34 D, from about 10 D to 30 D, or from 16 D to 28 D. The ranges shown in Table 21 correspond to possible expansions of the power progressive profile of Example 3.

TABLE 21

Range of values for coefficients describing a posterior power progression profile for different base powers

|  | Lower limit | Upper limit |
|---|---|---|
| R | −30 | −10 |
| k | −42 | 4 |
| $a_4$ | 0 | 0.05 |
| $a_6$ | −0.05 | 0 |
| $a_8$ | 0 | 0.01 |
| $a_{10}$ | −0.01 | 0 |
| $a_{12}$ | 0 | 1.0E−04 |

Figure 19:
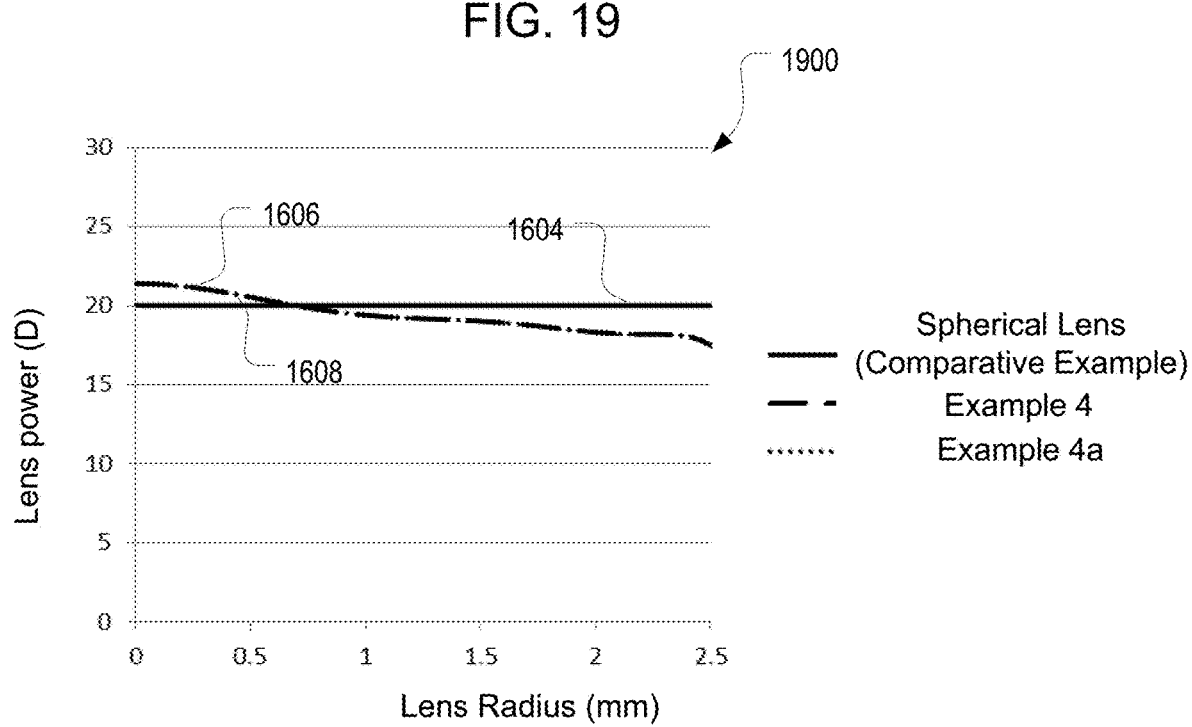
FIG. 19 illustrates power profiles of two example refractive, power progressive lenses positioned on the anterior and posterior sides of a lens, with reference to a spherical lens power profile.

Alternatively, the higher order aspheric power-progressive lens surface can be imposed on the anterior lens surface while producing the same or similar continuous power progression. Table 22, below, shows the parameters describing continuous power progressive lens surface disposed on an anterior surface of an ophthalmic lens. Example 4a corresponds to the anterior aspheric design, and Example 4 corresponds to the posterior design. FIG. 19 shows a graphical comparison 1900 between lens power profiles of Example 4 (1606), Example 4a (1608) and the monofocal spherical reference lens 1604. FIG. 19 illustrates that the power profiles of the posterior asphere Example 4 and its sibling anterior aspheric design Example 4a are virtually identical.

TABLE 22

Coefficients describing the power progression applied in the anterior optic in Example 4a

| Design | R | k | $a_4$ | $a_6$ | $a_8$ | $a_{10}$ | $a_{12}$ |
|---|---|---|---|---|---|---|---|
| Example 4a | 10.3 | 3.0E−03 | −8E−03 | 4E−03 | −1E−03 | 1E−04 | −7E−06 |

Table 23, below, describes a range of values for the parameters describing power progression refractive profiles on the anterior lens surface for a lens having a base power between 18 D and 20 D, when the posterior lens surface is spherical. A power progressive refractive profile with the features described herein can have a posterior radius between 7 and 13 mm. Similarly as for the posterior surface, the greater the radius of the anterior aspheric design, the less pronounced the power progression throughout the lens profile.

TABLE 23

Range of values for coefficients describing a power progression profile applied to an anterior side of a lens

|  | Lower limit | Upper limit |
|---|---|---|
| R | 7 | 13 |
| k | −1.5 | 0.05 |
| $a_4$ | −0.1 | 0.025 |
| $a_6$ | −0.05 | 0.025 |
| $a_8$ | −0.025 | 0.01 |
| $a_{10}$ | −0.001 | 0.001 |
| $a_{12}$ | −0.0001 | 0.0001 |

Combined Diffractive and Power Progressive Refractive Lenses

Embodiments disclosed herein can provide an extended depth of focus (EDF). In some embodiments, diffractive intraocular lenses described herein can also provide an EDF that results in a range of vision that covers distance, intermediate and/or near visual lengths with a better image quality than presently available multifocal lenses while mitigating certain dysphotopsia effects, such as glare or halo.

Methods of manufacture for lenses and lens profiles as disclosed herein, as well as methods of treatment utilizing said diffractive and refractive power-progressive lenses may include techniques described in, e.g., U.S. Pat. No. 9,335,563, entitled "MULTI-RING LENS, SYSTEMS AND METHODS FOR EXTENDED DEPTH OF FOCUS," which is hereby incorporated by reference.

Diffractive lenses can make use of a material having a given refractive index and a surface curvature which provide a refractive power. Diffractive lenses affect chromatic aberration. Diffractive lenses have a diffractive profile which confers the lens with a diffractive power or power profile that contributes to the overall depth of focus of the lens. The diffractive profile is typically characterized by a number of diffractive zones. When used for ophthalmic lenses these diffractive zones are typically annular lens zones, or echelettes, spaced about the optical axis of the lens. Each echelette may be defined by an optical zone, a transition zone between the optical zone and an optical zone of an adjacent echelette, and echelette geometry. The echelette geometry includes an inner and outer diameter and a shape or slope of the optical zone, a height or step height, and a shape of the transition zone. The surface area or diameter of the echelettes largely determines the diffractive power(s) of the lens and the step height of the transition between echelettes largely determines the light distribution between the different powers. Together, these echelettes form a diffractive profile. The diffractive profile affects ocular chromatic aberration. Chromatic aberration can be increased or decreased depending on the morphology of the echelettes that compose the diffractive profile. The modification of chromatic aberration can be at distance, intermediate, near and/or the complete range of vision provided by the diffractive profile.

A traditional multifocal diffractive profile on a lens may be used to mitigate presbyopia by providing two or more optical powers, for example, one for near vision and one for far vision. The hybrid diffractive/refractive lenses disclosed herein provide an extended depth of focus across a range of optical powers. The lenses may take the form of an intraocular lens placed within the capsular bag of the eye, replacing the original lens, or placed in front of the natural crystalline lens. The lenses may also be in the form of a contact lens.

In specific embodiments, the refractive profile and diffractive profile may be applied to the same side of the lens (e.g., both on a posterior surface of the lens, or both on an anterior surface of the lens); or may be applied on opposite surfaces (e.g., with the diffractive profile on the posterior surface and the refractive power-progressive profile on the anterior surface).

According to some embodiments, a lens combining a diffractive profile and an aspheric power-progressive profile may have multiple diffractive zones. For example, a central zone of the lens may have one or more echelettes at one step height and one phase delay, with a peripheral zone having one or more other echelettes at a different step height and/or phase delay. According to a specific example (see Table 24, below), the central zone can have three echelettes and the peripheral zone has 6, providing for a total number of 9 echelettes within a lens of about 5 mm diameter. In the example, the step height of the central zone is lower than in the peripheral zone. In an alternative embodiment, the step height of the central zone may be higher than in the peripheral zone. Alternatively, the step height may be the same throughout the lens profile.

According to embodiments, a refractive power progressive and a diffractive profile occupy an entire working area, or optical area, of the lens. The minimum optical area of an IOL has a radius of about 2 mm around the optical axis. In various embodiments, the optical area has a radius from about 2 mm to about 3 mm; or from about 2 mm to about 2.5 mm. In a preferred embodiment, both the refractive profile and the diffractive profile occupy the entire optical area.

Figure 20:
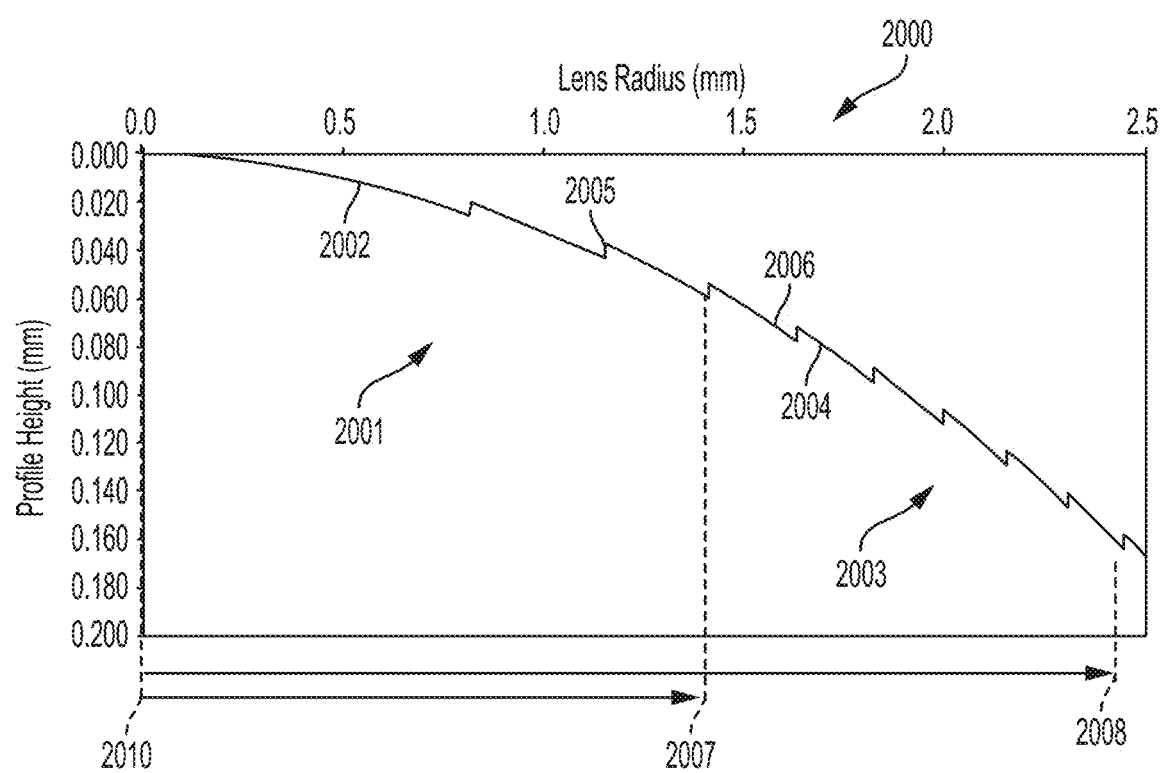
FIG. 20 is a graphical representation illustrating aspects of a diffractive component of a first combined aspheric refractive/diffractive lens profile, according to some embodiments.

FIG. 20 is a graphical representation illustrating a combined aspheric refractive/diffractive lens profile 2000 according to some embodiments. The refractive component of the combined profile is a high order asphere that results in a power progressive profile. The diffractive component of the combined profile contains sets of zones, e.g., a central zone 2001, and a peripheral zone 2003 that partially corrects for ocular chromatic aberrations.

The central zone 2001 in the example profile 2000 has three echelettes 2002 having the same, first step heights 2005. The peripheral zone 2003 has six echelettes 2004 having the same, second step heights 2006. The total number of echelettes, and the step heights of the echelettes in each zone, may vary. The central zone 2001 extends from a lens center 2010 to a first position 2007 and the peripheral zone 2004 extends from the first position 2007 to a second position 2008 defined in terms of the radius of the lens. The specific attributes of an example lens D1 (2000) are described below in Table 24:

TABLE 24

Diffractive Profile Parameters

| D1 | # of Echelettes | Phase Delay ($\lambda$) | Step Height ($\mu$m) | Extension of the zone (mm) |
|---|---|---|---|---|
| Central Zone | 3 | 1.3 | 5.3 (105) | 1.42 |
| Periphery | 6 | 1.366 | 5.6 (106) | 2.45 |

The diffractive profile in the example lens D1 has a phase delay between 1 and 2$\lambda$ for all of the echelettes. This phase delay has the effect of causing the diffractive profile to operate primarily in the first and second diffractive orders. As a consequence, the diffractive design partially corrects ocular chromatic aberration. Phase delay can pertain to a single echelette; or can be ascribed to a group of echelettes each having the same phase delay, where the group comprises a zone of the diffractive profile. Thus, phase delay can characterize single echelettes, groups of echelettes, or an entire profile.

According to various embodiments, the number of diffractive echelettes for a lens configured for a 5 mm pupil may range from 5 to about 14 echelettes. The first echelette boundary can be positioned at a radius of between 0.6 and 1.1 mm, with the remainder of the echelettes placed between the first echelette boundary and the lens periphery. The position of each subsequent echelette after the first echelette can be determined by the position of the first echelette multiplied by the square root of the respective echelette number.

Where the echelettes differ in phase delay between a central zone and a peripheral zone, the central zone can include between 1 and 5 echelettes, or between 1 and 3 echelettes. The phase shift of echelettes in the peripheral zone may be greater than 1$\lambda$ and smaller than 1.6$\lambda$, or between 1.2 and 1.4$\lambda$. The phase shift of the echelettes in the central zone may be smaller, greater, or in some cases the same as in the periphery. In some embodiments, the phase shifts of the central echelettes may be 0.1 to 0.5$\lambda$ smaller than, or greater than, the phase shifts of echelettes in the periphery. Alternatively, a central echelette or echelettes may have the same phase shift as echelettes in the periphery, while a remainder of the rings in the central zone have a greater or smaller phase shift than the echelettes in the periphery, e.g. by about 0.1 to about 0.5$\lambda$.

In alternative embodiments, the phase delay may be between 2 and 3$\lambda$. In such an embodiment, the diffractive profile operates between the second and third diffractive order. I such cases, the phase shifts of the peripheral zone should preferably be greater than 2$\lambda$ and smaller than 2.6$\lambda$, or between 2.2 and 2.4$\lambda$. The phase shift of the echelettes in the central zone may be smaller, greater, or in some cases the same as in the periphery. In some embodiments, the phase shifts of the central echelettes may be 0.1 to 0.5$\lambda$ smaller than, or greater than, the phase shifts of echelettes in the periphery. Alternatively, a central echelette or echelettes may have the same phase shift as echelettes in the periphery, while a remainder of the rings in the central zone have a greater or smaller phase shift than the echelettes in the periphery, e.g. by about 0.1 to about 0.5$\lambda$.

Light distribution is controlled by the step height between zones, such that a portion of the focusable light is directed to a distance focus, with most of the remainder of the light providing the extended depth of focus. The total light efficiency in the range of vision provided by the diffractive profile is approximately 93%. That efficiency results in a light loss of 7%, which is approximately 50% lower than a light loss typical for standard multifocal IOLs (which have light efficiencies of approximately 82%).

Figure 21:
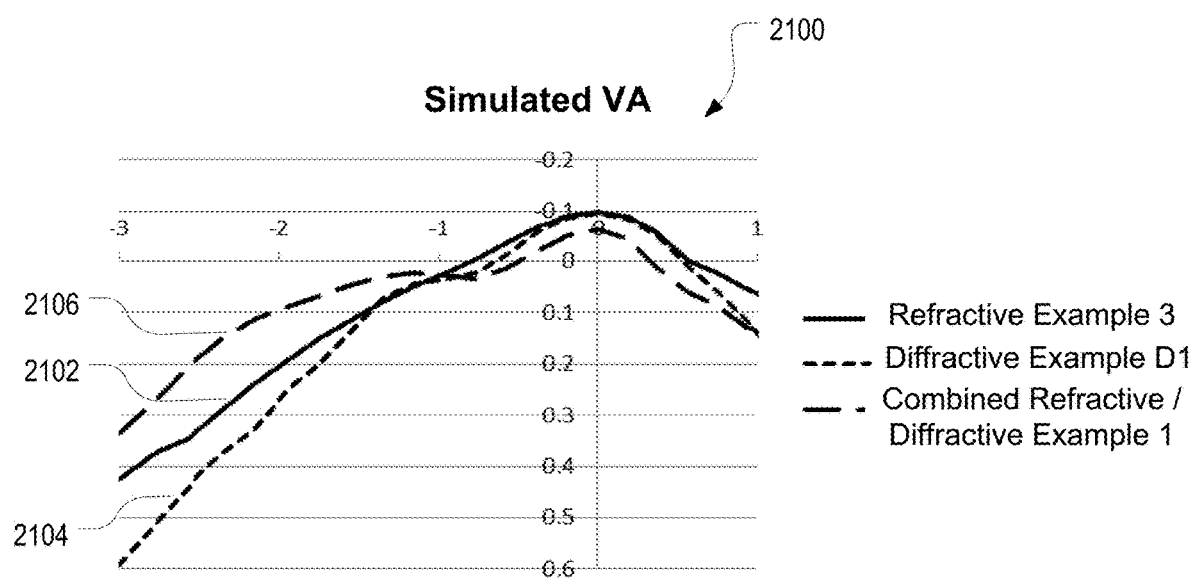
FIG. 21 shows simulated VA of a first example of a combined power progressive/diffractive extended depth of focus (EDF or EDOF) lens with reference to component lenses having a power progressive and having a diffractive profile, according to some embodiments.

According to some embodiments, a hybrid, combined diffractive/power progressive refractive lens includes a combination of a diffractive profile, similar to the diffractive profile described above with reference to Table 24, with a refractive power progressive profile, as described above with reference to, e.g., FIGS. 16-18. Performance of the hybrid or combined designs, as compared to a power-progressive refractive component (Example 3) and as compared to a diffractive ERV component (D1), is shown in the simulated VA curves 2100 of FIG. 21. FIG. 21 shows that the hybrid lens 2106 formed by a combination of a power-progressive refractive profile 2102 and diffractive profile 2104 provides a depth of focus that is larger than the depth of focus achievable with either of the individual refractive or diffractive profiles alone.

In alternative embodiments, different refractive power progressive profiles may be provided for combination with the aforementioned, or other, diffractive profiles. For example, the depth of focus of the combination can be controlled by providing a power progressive profile with a more or less pronounced power progression.

Figure 22:
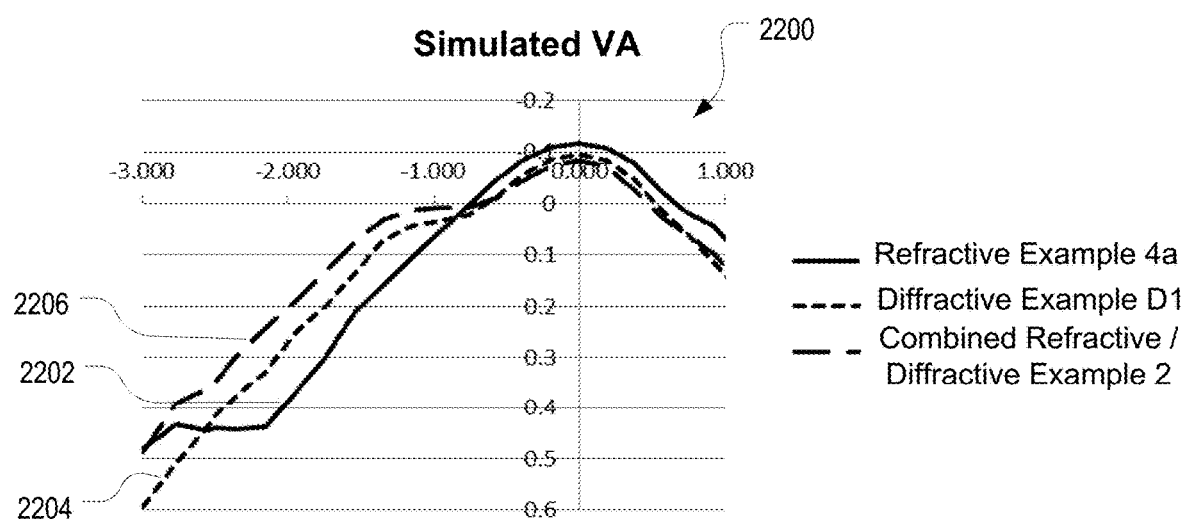
FIG. 22 shows simulated VA of a second example of a combined power progressive/diffractive extended depth of focus (EDF or EDOF) lens with reference to component lenses having a power progressive and having a diffractive profile, according to some embodiments.

For comparative purposes, FIG. 22 illustrates the simulated VA curves 2200 of example lenses and lens components Example 4a (the progressive power lens profile described above at Table 22) and D1 (the diffractive ERV lens profile described above in Table 24) alongside combined lenses utilizing D1 in combination with Example 4a. FIG. 22 shows that the hybrid combined lens profile 2206, which is formed by combining the refractive profile 2202 and diffractive profile 2204, provides a depth of focus that is larger than the depth of focus achievable with either of the individual refractive or diffractive profiles alone. However, the depth of focus of the combination 2206 is substantially smaller than for the hybrid, combined lens profile 2106 (FIG. 21). The longer depth of focus of the hybrid combined lens profile shown in FIG. 22 compared to that of FIG. 21 is provided by the steeper power progression described of the power progressive lens of Example 3 (FIG. 21).

Figure 23:
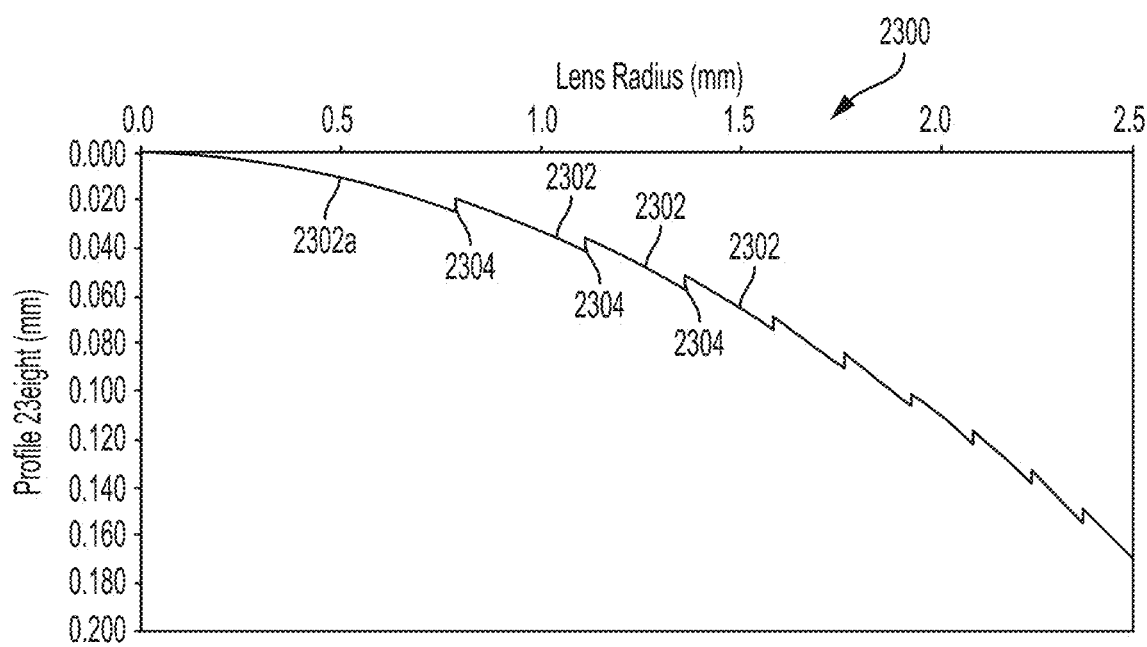
FIG. 23 is a graphical representation illustrating aspects of an alternative embodiment of a diffractive component of a combined aspheric refractive/diffractive lens profile according to some embodiments.

In an alternative embodiment, a lens combining a diffractive profile and an aspheric power-progressive profile may have diffractive echelettes with the same step height. For example, FIG. 23 is a graphical representation illustrating aspects of the diffractive component of a combined aspheric refractive/diffractive lens profile 2300 according to some embodiments. The example profile 2300 has nine echelettes 2302 having the same step heights 2304. In some specific embodiments, the first echelette 2302a has a boundary positioned at about 0.79 mm from the optic center of the lens. However, it will be understood that the position of the first echelette boundary, the total number of echelettes, and the step heights and position of the echelettes, may vary.

According to embodiments, the diffractive profile 2300 has a consistent phase delay through the optical zone.

According to some embodiments, the phase delay is larger than 1λ and smaller than 2λ, for all the echelettes. This profile provides for a diffractive profile that operates in predominantly in the first and second diffractive orders, so that the lens partially corrects ocular chromatic aberration.

Specific embodiments of combined diffractive/refractive power progressive lenses are described in terms of visual acuity simulations in FIGS. 24 and 25. According to one example, SM-1 is an example diffractive lens profile with a diffractive part that has nine echelettes with common phase delays of 1.366λ and step heights of 5.6 microns as shown below in Table 25. Alternative embodiments are also shown, i.e. SM-3, which is an example diffractive lens profile having a phase delay of 1.5, with step heights of 6.2 mm, respectively. The positions of the diffractive echelettes are the same for all embodiments presented in Table 25.

TABLE 25

Diffractive Profile Parameters

| Diffractive Profile | # of Echelettes | Phase Delay (λ) | Step Height (μm) |
|---|---|---|---|
| SM-1 | 9 | 1.366 | 5.6 |
| SM-3 | 9 | 1.5 | 6.2 |

In some (general) embodiments, phase delay can be larger than 1λ and smaller than 2λ. In specific embodiments, phase delay can range from about 1.1λ up to 1.6λ, or from 1.2 to 1.5λ. The number of echelettes is determined based on the desired geometry of each echelette and the available radius. The number of echelettes may vary from as few as 5 to up to 10 in some specific embodiments; or in certain embodiments up to 14. For example, for a lens configured for a pupil with a diameter of 5 mm, the number of echelettes may range between 5 and 14 echelettes. In specific embodiments, the first echelette may be positioned with an echelette boundary between 0.6 and 1.1 mm from a center of the lens, with a remainder of the echelettes placed according the position of the first echelette multiplied by the square root of the echelette number.

In an alternative embodiment, the phase delays of the diffractive echelettes may be between 2 and 3λ. In such cases, the diffractive profile operates between the second and third diffractive orders. In specific embodiments of lenses with echelettes having phase delays between 2 and 3λ, the ranges for the phase shifts of the echelettes is generally greater than 2λ and smaller than 2.6λ, or preferably between 2.2 and 2.5λ.

A hybrid, combined diffractive/power progressive refractive lens was developed by combining the diffractive profile described above with reference to Table 25 with the refractive power progressive profiles described with reference to FIGS. 16-19. Various diffractive profiles can be combined with the refractive power-progressive profile in this manner. For example, specific hybrid, combined diffractive/power progressive refractive lens profiles were developed (the combined profiles) by combining the diffractive profiles described above with reference to Table 25 with one or another of the refractive power progressive profiles described with reference to FIGS. 16-18.

For example, FIG. 24 shows simulated VA curves 2400 for the SM-1 diffractive profile 2404 with a comparative, simulated VA curve for a representative power-progressive refractive design (refractive only) power-progressive lens surface, Example 3 2402. The performance of the combined design 2406, which incorporates both profiles SM-1 and Example 3, exhibits a broader range of visual acuity in the near and intermediate visual range (i.e. a longer depth of focus) than either component part.

Combined profiles based on SM-1, and SM-3 each provide for slightly different distributions of light for distance vision n shown in Table 26, below:

TABLE 26

Diffractive Profile Light Distribution to Distance Range, and Total Light Efficiency in the Range of Vision

| | Distance | Range of Vision |
|---|---|---|
| SM-1 | 0.62 | 0.93 |
| SM-3 | 0.42 | 0.92 |

In Table 26, the SM-1 diffractive lens profile directs 62% of the focusable light to the distance focal range. The light efficiency in the range of vision provided by the diffractive profile is approximately 93%. That results in a light loss of 7%, which is approximately 50% lower than the light loss for a multifocal IOL operating in a similar range (which has a light efficiency of approximately 82%).

The alternate embodiments, SM-3, exhibit a different light distribution profile. SM-3, provides a greater distribution of light to extended depth of focus range (i.e., an extended range of vision including near and intermediate distances) than SM-1. In all the cases, the light efficiency in the total visual range (distance and extended depth of focus) is larger than that for traditional multifocal lenses.

For a given refractive power-progressive profile, the performance of the combination depends on the diffractive profile. For diffractive profiles with a greater light distribution at the extended depth of focus, near performance is further enhanced when combined with the refractive profile. For example, FIG. 25 shows simulated VA curves 2500 for various lenses incorporating the same power-progressive profile (Example 3) with differing diffractive profiles SM-1 (2406), and SM-3 (2506) in accordance with embodiments. For example, the combination diffractive/power progressive refractive lens using the diffractive profile SM-3, which has an increased light distribution to the extended depth of focus range, provides increased performance at the intermediate and near region. In contrast, the combination with SM-1 provides better distance performance but a slightly shorter depth of focus.

Figure 26:
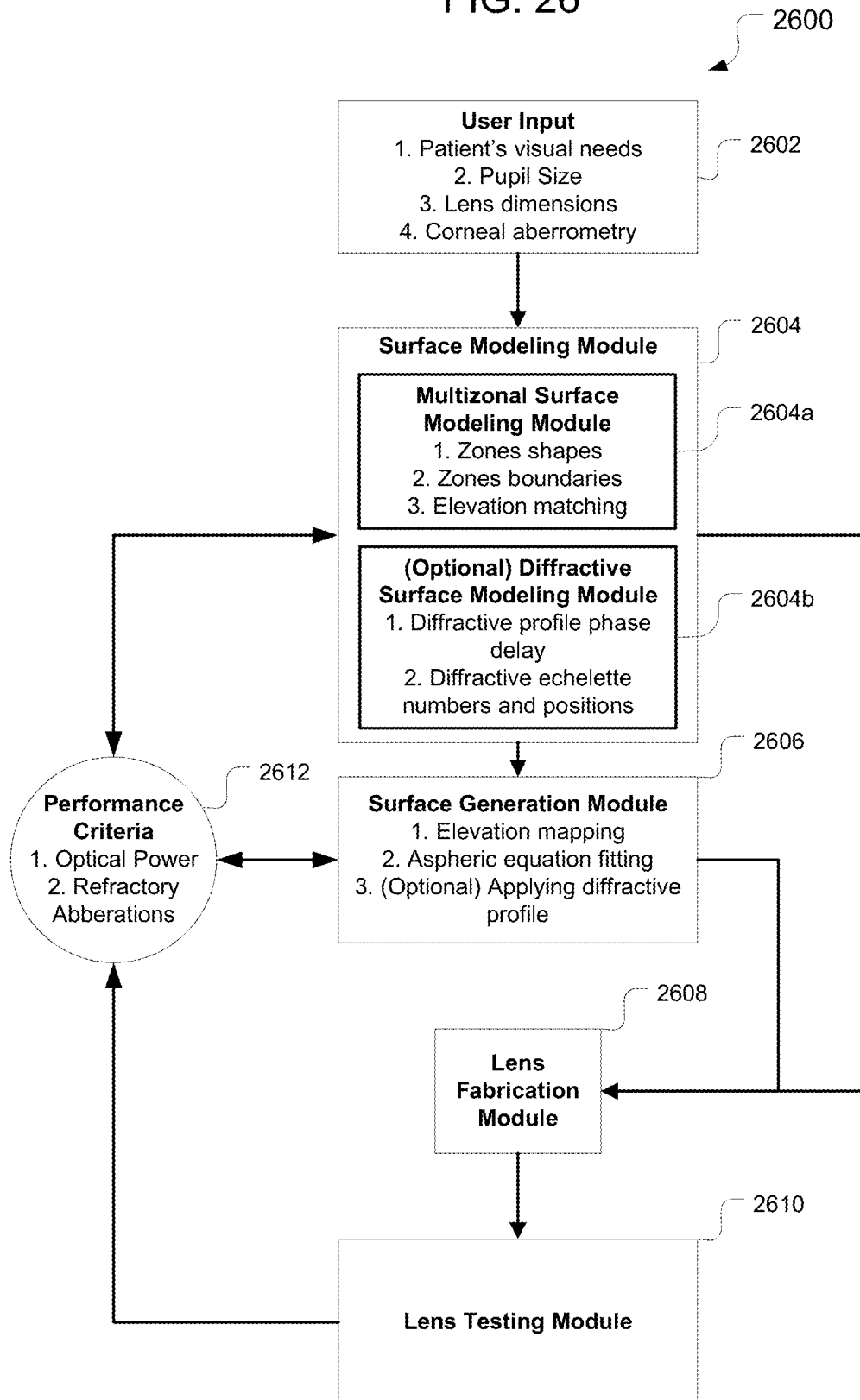
FIG. 26 is a simplified block diagram illustrating a system for generating a continuous progressive lens surface, in accordance with embodiments.

Systems and Methods for Determining Lens Shape:

FIG. 26 is a simplified block diagram illustrating a system 2600 for generating a continuous progressive lens surface, such as the continuous progressive lens surfaces 104 of FIG. 1 or 904 (FIG. 9), based on a multizonal surface, in accordance with embodiments. The system 2600 can be used for generating other continuous progressive lens surfaces as well, including lens surfaces configured for providing more than two or three optical regimes. The system 2600 may, in some cases, be used to generate a multizonal lens surface as an intermediate step to generating a continuous progressive lens surface. The system 2600 may also be used to produce IOLs conforming to a generated continuous progressive lens surface. In some embodiments, the system 2600 can be used to produce IOLs including a diffractive profile that is combined with a continuous power-progressive lens surface, either combined on the same surface (anterior or posterior) of the lens, or occupying opposite sides of the continuous progressive lens surface.

The system 2600 includes a user input module 2602 configured to receive user input defining aspects of an intraocular lens. Inputs to design an intraocular lens may include a patient's visual needs, corneal aberrations (or corneal topography, from which corneal aberrations can be retrieved), a pupil size performance, and lens dimensions, among other attributes. For example, the input can include a desired optical power profile for correcting impaired distance vision, a desired optical power profile for correcting impaired intermediate distance vision, a desired optical power profile for accommodating near distance vision, and any suitable combination of the above. In some cases, a desired optical power profile may relate to a patient's lifestyle, e.g., whether the patient prefers to participate in activities requiring predominantly distance vision, intermediate vision, or near vision without additional visual correction. A multifocal prescription can be calculated from a patient's visual needs. The multifocal prescription can include, for example, a preferred optical power or optical power profile for correcting far vision and an optical power or optical power profile for near vision. In some cases, a multifocal prescription can further include an optical power or optical power profile for correcting intermediate vision, which may fall between the optical powers or ranges of optical powers described above. The corneal aberrations (or corneal wave front aberrations) can include the higher order rotationally symmetrical aberrations of the cornea as a function of the pupil size. A pupil size performance can include a pupil diameter of a patient and the vision distance to be improved. These parameters can also be related to patient's life style or profession, so that the design incorporates patient's visual needs as a function of the pupil size. In some cases, parameters such as the asphericity of a peripheral region can be determined based on a function of the wave front aberrations and visual needs of the patient. Lens dimensions can include a preferred radius of the total lens, and may further include preferred thickness, or a preferred curvature of one or the other of the anterior surface and posterior surface of the lens.

A surface modeling module 2604 can receive information about the desired lens from the user input module 2604, and can determine aspects of a multizonal lens. According to some embodiments, the surface modeling module 2604 includes a multizonal surface modeling module 2604a, which can determine a multizonal lens profile according to a patient's visual needs. According to some embodiments, the surface modeling module 2604 can also include a diffractive surface modeling module 2604b, which can determine a diffractive lens profile also according to a patient's needs, preferably for combination with a refractive power-progressive profile.

For example, the multizonal surface modeling module 2604a can determine the shape of one or more zones of the multizonal lens, such as a curvature profile (e.g. spherical, aspheric) of each zone needed to fulfill the multifocal prescription, and the specific curvature of each zone. The curvature of the outer zone can be related to the biometry of the patient, while the curvature of the intermediate zones can be related with his visual needs in terms of intermediate and near performance. The asphericity of the outer zone can also be related to that of the patient's cornea, so that it either compensates patient's corneal spherical aberration or induces a certain amount of spherical aberration to help improving intermediate and near performance in mesopic conditions. The multizonal surface modeling module 2604a can further determine positions of zone boundaries. For example, the multizonal surface modeling module 2604a can define an outer diameter of the lens, i.e. the lens periphery, based on desired lens dimensions. The multizonal surface modeling module 2604a may further define a boundary between two or more optical zones based on the pupil size, the outer diameter of the lens, or both. In cases where there are more than two zones, the multizonal surface modeling module 2604a can define the respective inner and outer radii of each zone based also on the number of zones. The multizonal surface modeling module 2604a can also define heights of each respective zone, e.g. to match the heights of adjacent portions of each zone, such that an elevation profile of the lens is continuous.

The multizonal surface modeling module 2604a can be configured to generate performance criteria 2612, e.g. via modeling optical properties in a virtual environment. Performance criteria can include the match of the optical power profile of the multizonal lens with the desired optical power profile based on the multifocal prescription. The performance criteria can also include the severity of refractive aberrations caused by the multizonal surface. In some cases, the multizonal surface modeling module 2604a can provide an intraocular lens surface to an intraocular lens fabrication module for facilitating the production of a physical lens, which can be tested via an intraocular lens testing module 2610 for empirically determining the performance criteria 2612, so as to identify optical aberrations and imperfections not readily discerned via virtual modeling, and to permit iteration.

The multizonal surface modeling module 2604a can provide a multizonal surface to a surface generation module 2606, which can be configured to produce a smooth aspheric surface such as the continuous power progressive lens surface 104 (FIG. 1). The surface generation module 2606 can be configured to generate an elevation map of a multizonal lens surface, and can fit an aspheric equation of the form of Equation 1 to the elevation map via any suitable computational method for approximating an empirical dataset. In some cases, the aspheric equation can be fitted via a least-squares fitting method.

According to some embodiments, a diffractive surface modeling module 2604b can operate in tandem with the multizonal surface modeling module 2604a to generate a diffractive profile for combination with a refractive power progressive profile, according to the methods disclosed herein. The diffractive surface modeling module 2604b can define a diffractive profile having specific echelette configurations, i.e. echelette numbers, positions, step heights, and phase delays, according to a patient visual need as provided by the user input module 2602. By way of nonlimiting example, one such diffractive profile may be an diffractive EDF profile tuned to work in combination with a refractive power progressive profile. Performance criteria 2612 can be assessed by either or both of the multizonal surface modeling module 2604a and the diffractive surface modeling module 2604b.

As described above with respect to the surface modeling module 2604, the surface generation module 2606 can also be configured to generate performance criteria 2612. Performance criteria can include the match of the optical power profile of a continuous power progressive lens surface generated by the surface generation module 2606 with the original multizonal surface. The above performance criteria may be weighted over lens regions that are spatially separate from the optical zone step of the original lens. In some cases, the surface generation module 2606 can also provide a continuous power progressive lens surface to the lens fabrication module 2608 in order to produce an intraocular lens for testing by the lens testing module 2610, so as to identify optical aberrations, visual artifacts and imperfections not readily discerned via virtual modeling, and to permit iteration. Iteration can include modifying parameters of the fitting step (e.g., a degree of fit, a maximum order of terms of the fitting equation, a number and selection of positions chosen for approximating the fit), and can also include iteratively changing parameters of the multizonal surface at the multizonal surface modeling module 2604.

Figure 27:
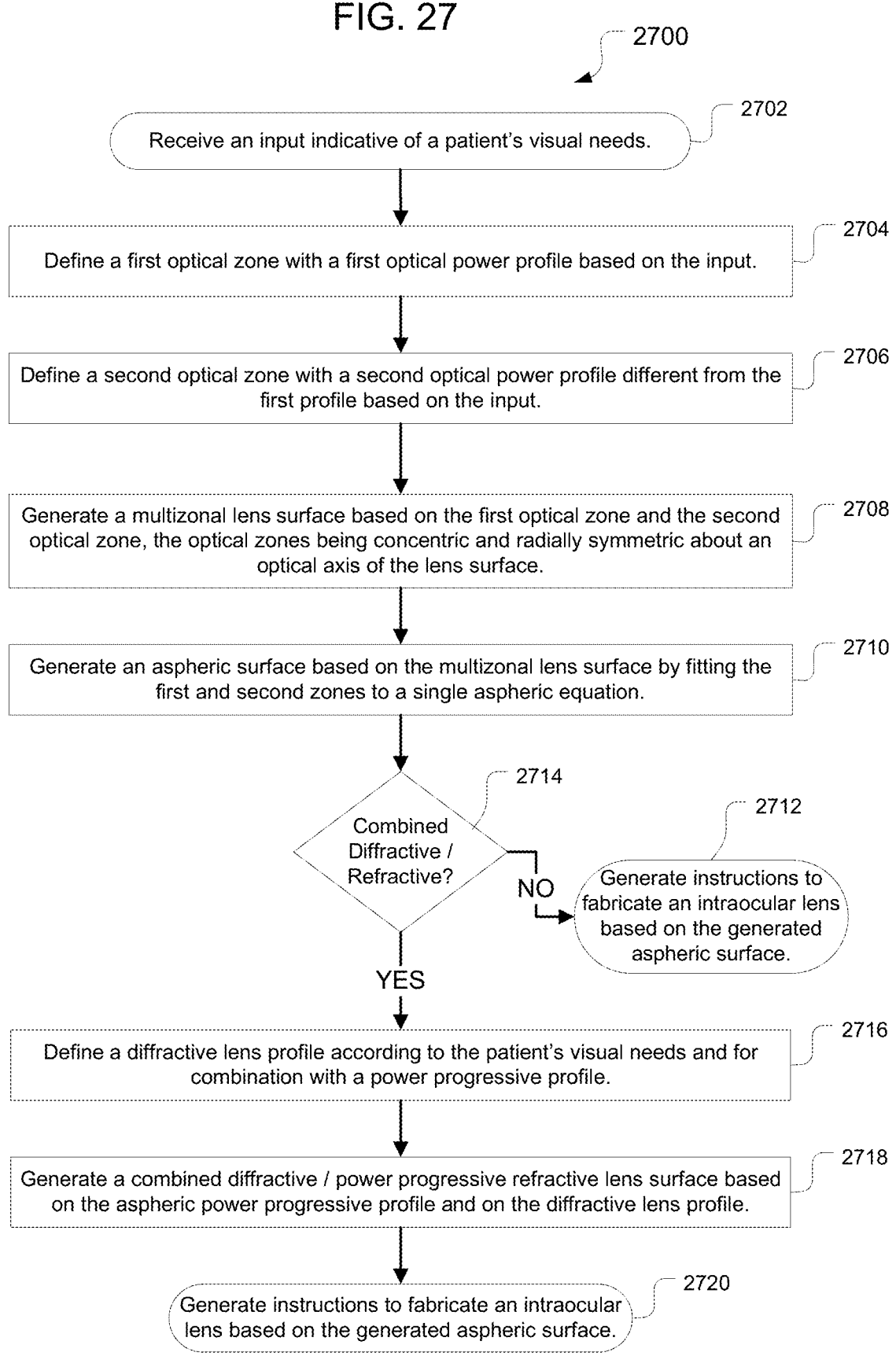
FIG. 27 illustrates an example process for generating a continuous progressive lens surface.

FIG. 27 is an example process 2700 for generating a continuous power progressive lens surface, in accordance with embodiments. The process 2700 may be implemented in conjunction with, for example, the system 2700 shown in FIG. 27. Some or all of the process 2700 (or any other processes described herein, or variations, and/or combinations thereof) may be performed under the control of one or more computer systems configured with executable instructions and may be implemented as code (e.g., executable instructions, one or more computer programs, or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

The process 2700 includes receiving an input indicative of a patient's visual needs (act 2702). The input can include, e.g., a desired optical power profile for correcting impaired distance vision, a desired optical power profile for correcting impaired intermediate vision, a desired optical power profile for accommodating near vision, and any suitable combination of the above. Next, a first optical zone can be defined according to a first optical power profile indicated by the multifocal lens prescription (act 2704). For example, the first zone can have a power profile suitable for correcting near and/or intermediate vision (i.e. a high relative power) and can be defined to include the center of the lens and extend to an outer perimeter of the first zone. The diameter defining the outer perimeter of the first zone is sized such that a patient seeing through the lens would see light incident through the first zone as well as light incident from outside the first zone. Next, a second optical zone can be defined according to a second optical power profile also indicated by the multifocal lens prescription (act 2706). In some cases, the second optical zone may be related to distance vision (i.e. a power profile for providing distance vision). In some cases, the second optical zone may have an aspheric profile suitable for correcting the corneal spherical aberration.

Next, the first and second optical zones can be merged to form a single multizonal surface (act 2708). A diameter defining the first optical zone extends to an interior edge of the second optical zone, and an outer diameter of the second optical zone may extend to a periphery of the lens. However, in some cases, additional optical add zones may be provided beyond the second. Generally, the first and second optical zones are defined as concentric and radially symmetric about the optical axis of the lens, with the second optical zone bounding the first optical zone. The relative heights of the first optical zone and second optical zone are adjusted such that an elevation of the outer perimeter of the first optical zone matches an elevation of the inner perimeter of the second optical zone. If additional zones are included, then each successive outer perimeter can be matched with each successive inner perimeter to generate a continuous elevation profile from the center of the lens to the lens periphery.

The multizonal surface can then be fitted to a new, unique and continuous aspheric surface which approximates attributes of the zones of the multizonal surface (act 2710). In some cases, fitting the multizonal surface to the continuous aspheric surface can include generating an elevation map of the multizonal surface, and performing a computational fitting based on a high-order aspherical lens equation like Equation 1, reproduced below, in which various high-order coefficients (e.g. $a_{10}$, $a_{12}$) are nonzero.

$$Z = \frac{cr^2}{1 + \sqrt{1 - (k+1)c^2 r^2}} + a_2 r^2 + a_4 r^4 + a_6 r^6 + a_8 r^8 + a_{10} r^{10} + a_{12} r^{12}$$

However, various other methods of fitting a high-order aspheric equation to the multizonal surface are possible within the scope of this disclosure. The final surface generated by the process 2700 can be characterized by a continuous function, such that a slope of an elevation map describing the generated surface is also continuous.

Where a purely refractive power-progressive lens is desired (i.e., not a combined diffractive/refractive lens) (act 2714), the system can generate instructions to fabricate an intraocular lens based on the generated aspheric surface (act 2712). However, in cases where a combined, or hybrid, diffractive/refractive power progressive lens is desired, the system can further define a diffractive lens profile according to the patient's visual needs and for combination with a power progressive profile (act 2716). In some cases, the diffractive profile may be defined for addition to a known power progressive profile; but in other cases, the specific diffractive profile and the specific power progressive refractive profile may be generated in an opposite order, or by an iterative process that incrementally adjusts both profiles to achieve the desired visual correction. A combined diffractive/power progressive refractive lens surface can then be generated based on the aspheric power-progressive profile and on the diffractive profile (act 2718). This generation can include generating a lens surface that has both the diffractive and refractive power progressive components on the same lens surface (e.g., posterior or anterior surface), or may provide a total lens surface having the respective components positioned on opposite surfaces from each other. The surface features defined by the diffractive profile (e.g., diffractive echelettes) overlap with the features defined by the refractive power-progressive profile (e.g., the aspheric surface). The system can then generate instructions to fabricate an intraocular lens based on the generated combined diffractive/power progressive refractive lens surface (act 2720).

Additional Embodiments:

In accordance with various embodiments, methods herein disclosed may be applied for generating a wide variety of useful progressive in power refractive lens designs. The aspheric power progressive surface may be applied for the anterior and posterior surface of the lens alternatively. Although several designs are included herein, changes in the specific parameters defining each zone, as well as the number of zones and the degree of spherical aberration may provide lens designs tailored for a variety of uses, e.g. choosing optical performance for specific distances, depths of focus, or other visual needs, in accordance with embodiments.

In accordance with various embodiments, lens surfaces as disclosed herein may be applied to any suitable existing IOL design. Suitable IOL designs can include toric, monofocal, multifocal, extended range of vision, and refractive-diffractive lenses, and combinations thereof. In some cases, with suitable translation to a corresponding optical plane, methods of determining a lens shape can also be applied to corneal refractive procedures. In alternative embodiments, designs herein disclosed may also be applied to any suitable aspheric optical surface, e.g. IOLs, corneal inlays, and corneal onlays.

In various embodiments, diffractive designs can be added to lenses generated according to the techniques described above. Suitable diffractive designs can include designs for controlling chromatic aberration, to generate multifocal effects, and/or to extend depth of focus.

Figure 28:
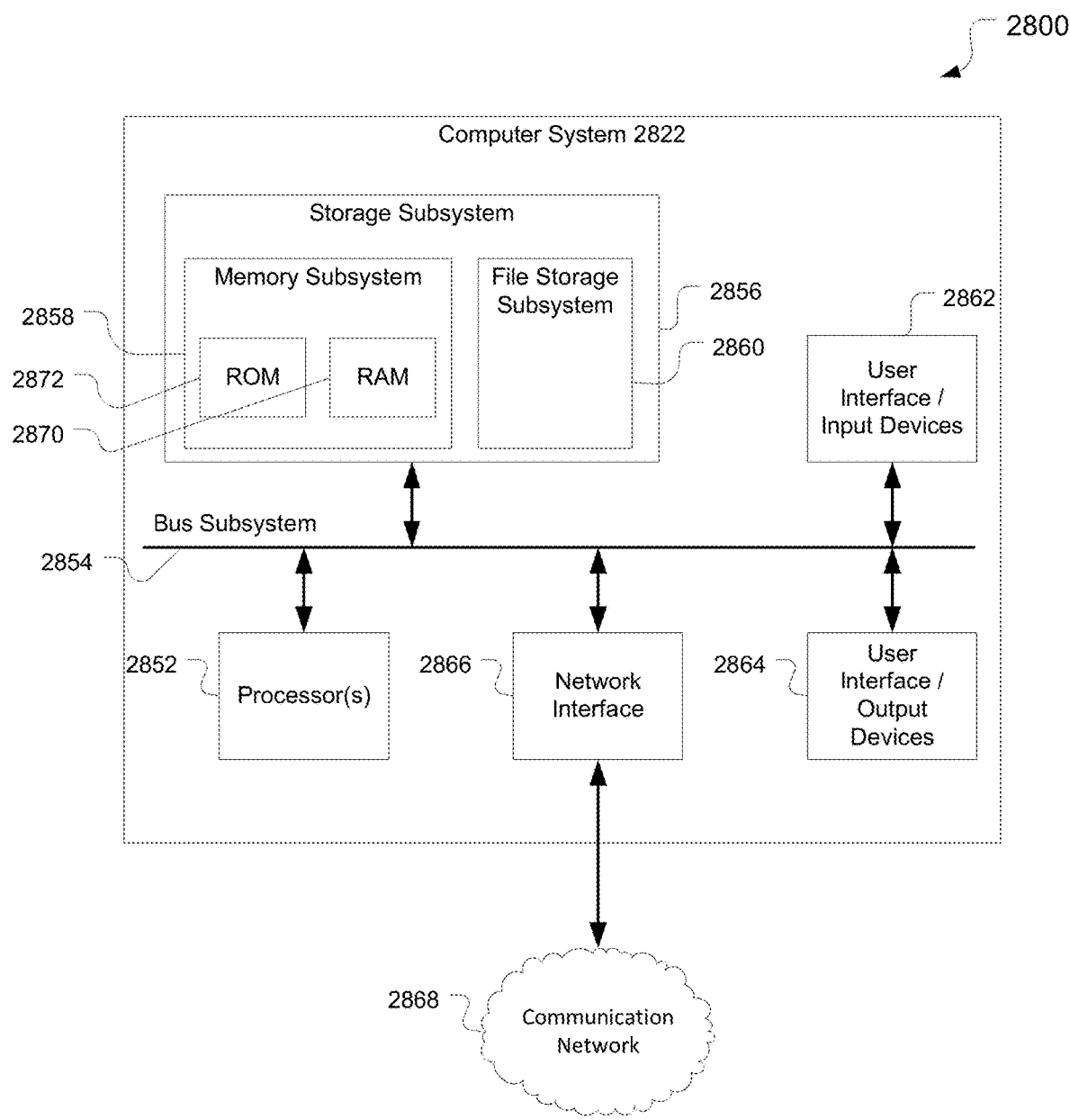
FIG. 28 illustrates an example computing environment for facilitating the systems and processes of FIGS. 26 and 27.

Computational Methods:

FIG. 28 is a simplified block diagram of an exemplary computing environment 2800 that may be used by systems for generating the continuous progressive lens surfaces of the present disclosure. Computer system 2800 typically includes at least one processor 2852 which may communicate with a number of peripheral devices via a bus subsystem 2854. These peripheral devices may include a storage subsystem 2856 comprising a memory subsystem 2858 and a file storage subsystem 2860, user interface input devices 2862, user interface output devices 2864, and a network interface subsystem 2866. Network interface subsystem 2866 provides an interface to outside networks 2868 and/or other devices, such as the lens fabrication module 2608 or lens testing module 2610 of FIG. 26. In some cases, some portion of the above-referenced subsystems may be available in a diagnostics device capable of measuring the biometric inputs required for calculating attributes such as base power.

User interface input devices 2862 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 2862 will often be used to download a computer executable code from a tangible storage media embodying any of the methods of the present invention. In general, use of the term "input device" is intended to include a variety of conventional and proprietary devices and ways to input information into computer system 2822.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety 20 of conventional and proprietary devices and ways to output information from computer system 2822 to a user.

Storage subsystem 2856 can store the basic programming and data constructs that provide the functionality of the various embodiments of the present invention. For example, a database and modules implementing the functionality of the methods of the present invention, as described herein, may be stored in storage subsystem 2856. These software modules are generally executed by processor 2852. In a distributed environment, the software modules may be stored on a plurality of computer systems and executed by processors of the plurality of computer systems. Storage subsystem 2856 typically comprises memory subsystem 2858 and file storage subsystem 2860. Memory subsystem 2858 typically includes a number of memories including a main random access memory (RAM) 2870 for storage of instructions and data during program execution.

Various computational methods discussed above, e.g. with respect to generating a fitted aspheric lens surface based on a multizonal lens surface, may be performed in conjunction with or using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of skill in the art, such as the Oxford Dictionary of Biochemistry and Molecular Biology (Ed. Anthony Smith, Oxford University Press, Oxford, 2004).

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

All references, including patent filings (including patents, patent applications, and patent publications), scientific journals, books, treatises, technical references, and other publications and materials discussed in this application, are incorporated herein by reference in their entirety for all purposes.

Aspects of the disclosure can be modified, if necessary, to employ the systems, functions, and concepts of the above references and application to provide yet further embodiments of the disclosure. These and other changes can be made to the disclosure in light of the detailed description.

Specific elements of any foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

While the above provides a full and complete disclosure of exemplary embodiments of the present invention, various modifications, alternate constructions and equivalents may be employed as desired. Consequently, although the embodiments have been described in some detail, by way of example and for clarity of understanding, a variety of modifications, changes, and adaptations will be obvious to those of skill in the art. Accordingly, the above description and illustrations should not be construed as limiting the invention, which can be defined by the appended claims.

What is claimed is:

1. A radial power-progressive lens, comprising:
a lens surface defined by a continuous aspheric function;
a first region of the lens approximating a first optical regime; and
a second region of the lens approximating a second optical regime; wherein
the first region comprises a first range of optical power values and the second optical regime comprises a second range of optical power values different from the first range,
the first and second regions are radially symmetric and concentric about an optical axis of the lens, the second region being disposed around the first region,
the first and second regions are merged by the continuous aspheric lens function such that a power profile of the lens from a center of the lens to a periphery of the lens is continuous,
the second region comprises a peripheral zone extending from an inner diameter of the second region to an outer periphery of the lens,
the lens surface can be described according to the following equation:

$$Z = \frac{cr^2}{1+\sqrt{1-(k+1)c^2r^2}} + a_2r^2 + a_4r^4 + a_6r^6 + a_8r^8 + a_{10}r^{10} + a_{12}r^{12},$$

and
at least the r, k, $a_4$, $a_6$, and $a_8$ terms are nonzero.

2. The lens of claim 1, wherein the second region approximates an aspheric optical zone having a base power, and wherein the first region is configured to generate higher relative power with respect to the second region.

3. The lens of claim 2, wherein the first region is further configured to approximate a spherical lens surface across at least a subset of the first region.

4. The lens of claim 1, wherein the first range of optical power values is higher than the second range of optical power values.

5. The lens of claim 1, wherein the continuous aspheric lens function approximates a first lens shape and a second lens shape different from the first lens shape, the first optical regime approximating the first lens shape and the second optical regime approximating the second lens shape.

6. The lens of claim 1, wherein the continuous aspheric lens function approximates a spherical lens surface and an aspherical lens surface, the first optical regime approximating the spherical lens surface and the second optical regime approximating the aspherical lens surface.

7. The lens of claim 1, wherein the continuous aspheric lens function merges a first curvature of an outer periphery of the first region and a second curvature of an inner periphery of the second region such that the first optical regime transitions smoothly into the second optical regime.

8. The lens of claim 1, wherein the first region comprises an aspheric approximation of a spherical lens curvature.

9. The lens of claim 1, wherein the first region is spherical.

10. The lens of claim 1, wherein the first region has a different power than a base power of the lens.

11. The lens of claim 1, wherein the first region is configured to generate a different range of power values with respect to the second region, and the first range of power values varies in magnitude from a first peak power near the optical axis to a first peripheral optical power near a boundary of the first region, the peak optical power being higher than the peripheral optical power.

12. The lens of claim 1, wherein the peripheral zone is aspheric.

13. The lens of claim 1, wherein at least the $a_{10}$ and $a_{12}$ terms are not zero.

14. The lens of claim 1, wherein the lens has a range of optical base powers from 5 D to 34 D, the lens surface being defined according to:
the 'r' term ranging from 4 to 29;
the 'k' term ranging from −3 to 13;
the '$a_4$' term ranging from −0.02 to 0;
the '$a_6$' term ranging from 0 to 0.01;
the '$a_8$' term ranging from −0.003 to 0;
the '$a_{10}$' term ranging from 0 to 0.0003; and
the '$a_{12}$' term ranging from −1.0 E −04 to 0.

15. The lens of claim 1, wherein the periphery of the lens corrects for corneal spherical aberration.

16. The lens of claim 1, wherein the first optical regime corresponds to a first prescription configured for improving at least one of near and intermediate vision.

17. The lens of claim 1, wherein a first peak value of the first range of optical power values is at least one diopter greater than an optical power of the second range of optical power values.

18. The lens of claim 1, wherein the first region has a diameter between 0.25 and 2 mm.

19. The lens of claim 1, wherein the second region has an inner diameter of less than or equal to 2 mm.

20. The lens of claim 1, further comprising a third region, the third region being radially symmetric and disposed around the second region and comprising a third optical regime comprising a third range of optical powers that is different from the first range and the second range.

21. The lens of claim 20, wherein the third region extends from a periphery of the second region to an outer perimeter of the lens.

22. The lens of claim 1, further comprising:
a diffractive surface that affects chromatic aberration.

23. The lens of claim 1, further comprising a spherical posterior surface.

24. The lens of claim 1, further comprising an aspheric posterior surface.

25. The lens of claim 1, wherein the lens comprises an intraocular implant.

26. The lens of claim 1, wherein the peripheral zone corrects asymmetric higher order aberrations.

27. The lens of claim 1, further comprising a toric posterior surface.

28. The lens of claim 1, further comprising a toric anterior surface.

29. The lens of claim 1, further comprising two principal meridians with different base powers.

30. The lens of claim 29, wherein the lens correct corneal astigmatism.

31. The lens of claim 1, further comprising one or more support elements configured to secure the lens to a patient's eye.

32. The lens of claim 1, further comprising a plurality of additional regions respectively configured to provide a plurality of additional optical regimes, each successive region of the plurality of additional regions being concentric about the center of the lens and being disposed around the first region, and each optical regime of the plurality of additional optical regimes being different from each other optical regime.

33. The lens of claim 32, wherein the plurality of additional regions comprises up to 8 additional regions.

34. A radial power-progressive lens, comprising:
a lens surface defined by a continuous aspheric function;
a first region of the lens approximating a first optical regime; and
a second region of the lens approximating a second optical regime; wherein
the first region comprises a first range of optical power values and the second optical regime comprises a second range of optical power values different from the first range,
the first and second regions are radially symmetric and concentric about an optical axis of the lens, the second region being disposed around the first region,
the first and second regions are merged by the continuous aspheric lens function such that a power profile of the lens from a center of the lens to a periphery of the lens is continuous,
the first region is configured to generate a different range of power values with respect to the second region, and the first range of power values varies in magnitude from a first peak power near the optical axis to a first peripheral optical power near a boundary of the first region, the peak optical power being higher than the peripheral optical power, and
the first range of power values of the first zone respect to the base power varies from approximately 1.75 diopters to approximately 0 diopters.

35. A radial power-progressive lens, comprising:
a lens surface defined by a continuous aspheric function;
a first region of the lens approximating a first optical regime; and
a second region of the lens approximating a second optical regime; wherein
the first region comprises a first range of optical power values and the second optical regime comprises a second range of optical power values different from the first range,
the first and second regions are radially symmetric and concentric about an optical axis of the lens, the second region being disposed around the first region,
the first and second regions are merged by the continuous aspheric lens function such that a power profile of the lens from a center of the lens to a periphery of the lens is continuous,
the first region is configured to generate a different range of power values with respect to the second region, and the first range of power values varies in magnitude from a first peak power near the optical axis to a first peripheral optical power near a boundary of the first region, the peak optical power being higher than the peripheral optical power, and
the first range of power values of the first zone respect to the base power varies from approximately 3.5 diopters to approximately 0 diopters.

* * * * *